US009763836B2

(12) United States Patent
Kawka et al.

(10) Patent No.: US 9,763,836 B2
(45) Date of Patent: Sep. 19, 2017

(54) APPARATUSES AND METHODS FOR MAKING ABSORBENT ARTICLES

(71) Applicant: The Procter & Gamble Company, Cincinnati, OH (US)

(72) Inventors: Paul Anthony Kawka, Kelso Township, IN (US); Uwe Schneider, Cincinnati, OH (US); Gary Dean LaVon, Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 381 days.

(21) Appl. No.: 14/635,189

(22) Filed: Mar. 2, 2015

(65) Prior Publication Data

US 2015/0250655 A1 Sep. 10, 2015

Related U.S. Application Data

(60) Provisional application No. 61/947,628, filed on Mar. 4, 2014.

(51) Int. Cl.
*B32B 37/00* (2006.01)
*A61F 13/15* (2006.01)
(Continued)

(52) U.S. Cl.
CPC .. *A61F 13/15764* (2013.01); *A61F 13/15593* (2013.01); *A61F 13/15723* (2013.01);
(Continued)

(58) Field of Classification Search
CPC .......... A61F 13/15634; A61F 13/15658; A61F 13/15723; A61F 13/15731;
(Continued)

(56) References Cited

U.S. PATENT DOCUMENTS 3,860,003 A 1/1975 Buell
4,610,678 A 9/1986 Weisman et al.
(Continued)

FOREIGN PATENT DOCUMENTS

WO WO 2004/014277 2/2004
WO WO 2010/141302 A1 12/2010

OTHER PUBLICATIONS

PCT/US2015/018437 International Search Report, dated May 28, 2015, 11 pages.

*Primary Examiner* — George Koch
(74) *Attorney, Agent, or Firm* — Charles R. Matson

(57) ABSTRACT

The present disclosure relates to methods and apparatuses for controlling the relative placement of advancing substrates and discrete components in diaper converting lines. The diapers may each include a chassis connected with front and back elastic belts. In controlling the relative placement of these elements during the assembly process, a controller may change the machine direction speed and/or position of certain elements and cross direction speed and/or position of other elements such as the advancing substrates and components in order to help achieve proper placement and orientation. During the assembly process, the registration features are detected, and a controller may change the machine direction speeds of the advancing elastic laminates and/or chassis and/or may change the cross directional and/or machine direction position of the advancing elastic laminates and/or chassis.

29 Claims, 11 Drawing Sheets

(51) Int. Cl.
*B32B 37/02* (2006.01)
*B32B 37/18* (2006.01)
*B32B 38/00* (2006.01)
*B32B 38/18* (2006.01)
*A61F 13/496* (2006.01)

(52) U.S. Cl.
CPC ...... *A61F 13/15772* (2013.01); *A61F 13/496* (2013.01); *B32B 37/0046* (2013.01); *B32B 37/02* (2013.01); *B32B 37/18* (2013.01); *B32B 38/0004* (2013.01); *B32B 38/185* (2013.01); *B32B 2307/50* (2013.01); *B32B 2555/02* (2013.01); *Y10T 156/10* (2015.01); *Y10T 156/108* (2015.01)

(58) Field of Classification Search
CPC .......... A61F 13/15764; A61F 13/15772; A61F 2013/15788; A61F 2013/15821; B32B 37/0046; B32B 37/370076; B32B 38/06; B32B 38/18; B32B 41/00; B32B 2037/243; B32B 2037/726; B32B 2535/00
See application file for complete search history.

(56) References Cited

U.S. PATENT DOCUMENTS

| | | |
|---|---|---|
| 4,673,402 A | 6/1987 | Weisman et al. |
| 4,695,278 A | 9/1987 | Lawson |
| 4,704,115 A | 11/1987 | Buell |
| 4,795,454 A | 1/1989 | Dragoo |
| 4,834,735 A | 5/1989 | Alemany et al. |
| 4,888,231 A | 12/1989 | Angstadt |
| 4,909,803 A | 3/1990 | Aziz et al. |
| 5,286,543 A | 2/1994 | Ungpiyakul et al. |
| 5,359,525 A | 10/1994 | Weyenberg |
| 5,562,646 A | 10/1996 | Goldman et al. |
| 5,599,335 A | 2/1997 | Goldman et al. |
| 5,628,097 A | 5/1997 | Curro et al. |
| 5,669,894 A | 9/1997 | Goldman et al. |
| 5,916,661 A | 6/1999 | Curro et al. |
| 6,107,539 A | 8/2000 | Palumbo et al. |
| 6,444,064 B1 | 9/2002 | Henry et al. |
| 6,545,197 B1 | 4/2003 | Mueller et al. |
| 6,790,798 B1 | 9/2004 | Suzuki |
| 6,801,828 B2 | 10/2004 | Popp et al. |
| 6,820,022 B2 | 11/2004 | Popp et al. |
| 6,955,733 B2 | 10/2005 | Miller et al. |
| 7,123,981 B2 | 10/2006 | Dollevoet et al. |
| 7,569,039 B2 | 8/2009 | Matsuda et al. |
| 7,587,966 B2 | 9/2009 | Nakakado et al. |
| 8,145,343 B2 | 3/2012 | Debruler et al. |
| 8,145,344 B2 | 3/2012 | Debruler et al. |
| 8,244,393 B2 | 8/2012 | McLaughlin et al. |
| 2004/0083018 A1* | 4/2004 | Dollevoet ......... A61F 13/15772 700/109 |
| 2004/0097895 A1 | 5/2004 | Busam et al. |
| 2004/0122391 A1 | 6/2004 | Franklin |
| 2004/0158212 A1 | 8/2004 | Ponomarenko et al. |
| 2005/0067083 A1* | 3/2005 | Vergona ............ A61F 13/15772 156/64 |
| 2005/0107764 A1 | 5/2005 | Matsuda et al. |
| 2009/0312730 A1 | 12/2009 | LaVon et al. |
| 2010/0305738 A1* | 12/2010 | DeBruler .......... A61F 13/15772 700/105 |
| 2010/0305739 A1* | 12/2010 | DeBruler .......... A61F 13/15772 700/108 |
| 2012/0061015 A1 | 3/2012 | LaVon et al. |
| 2012/0061016 A1 | 3/2012 | LaVon et al. |
| 2013/0152360 A1* | 6/2013 | Schoultz ................ B65H 39/14 29/428 |
| 2013/0255861 A1 | 10/2013 | Schneider et al. |
| 2013/0255862 A1 | 10/2013 | Schneider et al. |
| 2013/0255863 A1 | 10/2013 | LaVon et al. |
| 2013/0255864 A1 | 10/2013 | Schneider et al. |
| 2013/0255865 A1 | 10/2013 | Brown et al. |
| 2013/0270065 A1 | 10/2013 | Papsdorf et al. |
| 2013/0270066 A1 | 10/2013 | Papsdorf et al. |
| 2013/0270067 A1 | 10/2013 | Papsdorf et al. |
| 2013/0270069 A1 | 10/2013 | Papsdorf et al. |
| 2014/0112751 A1 | 4/2014 | Schneider et al. |
| 2015/0111714 A1 | 4/2015 | Takeuchi et al. |

\* cited by examiner

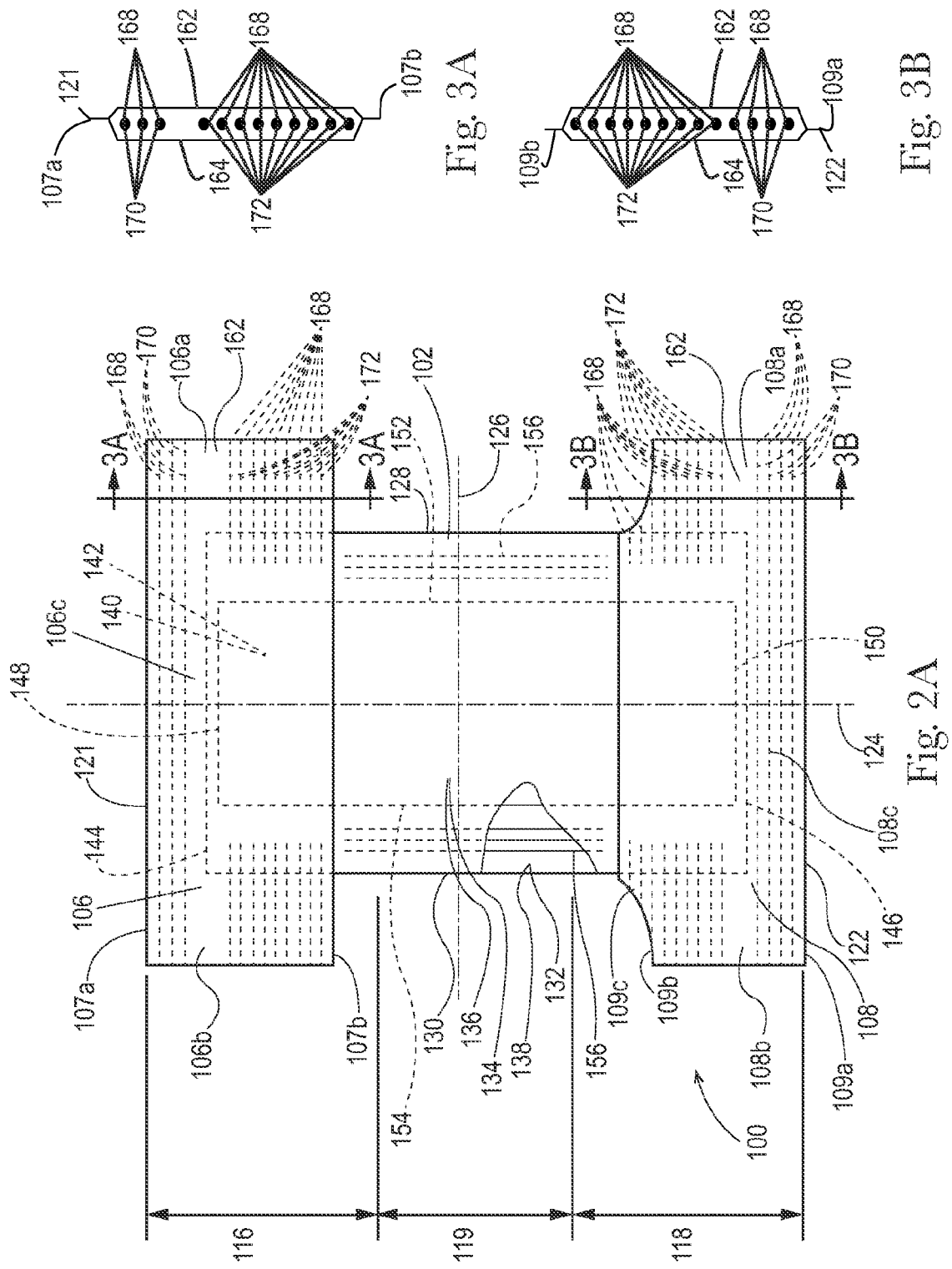

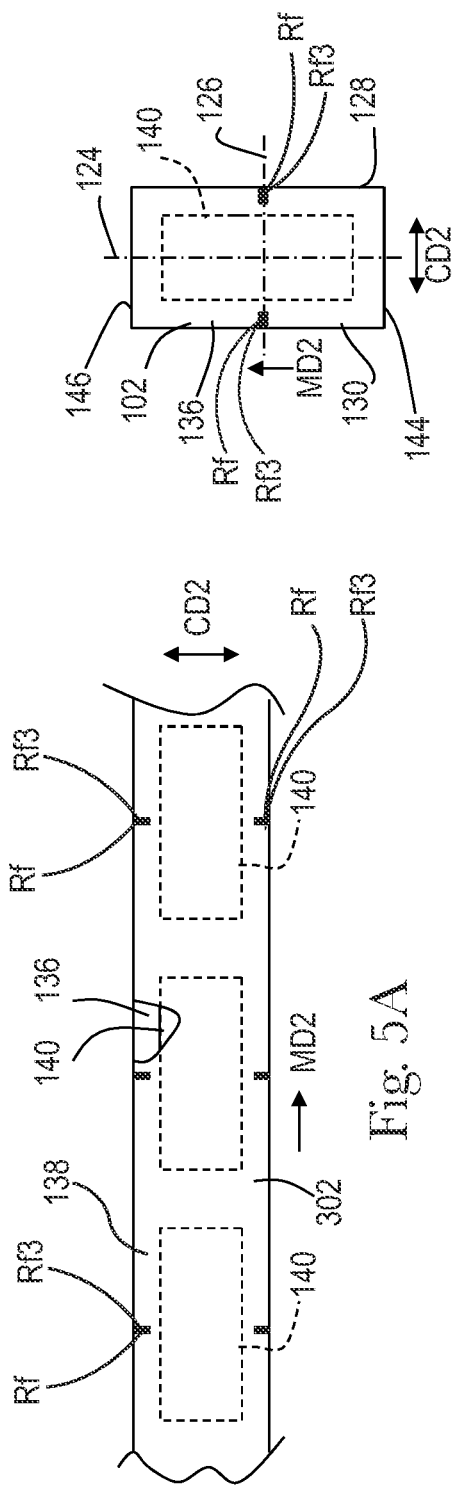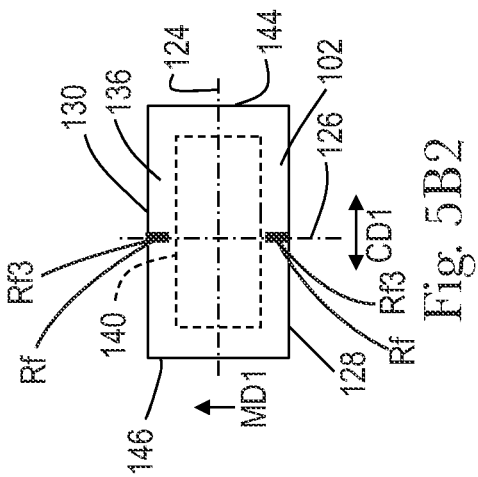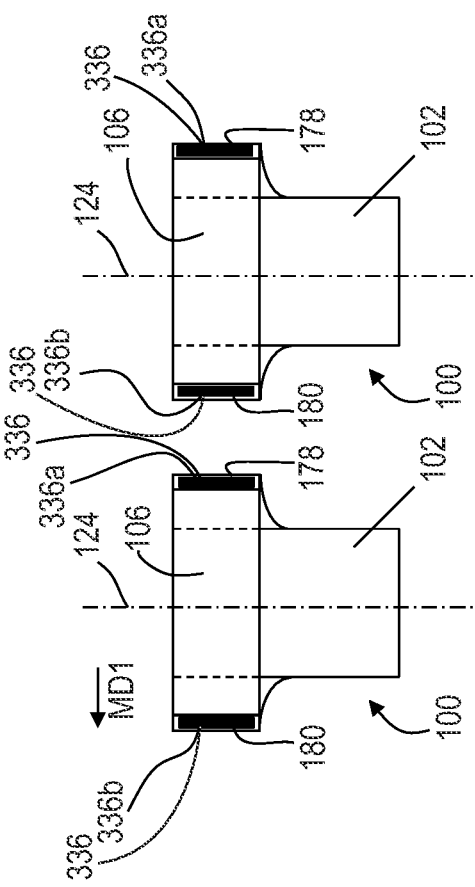

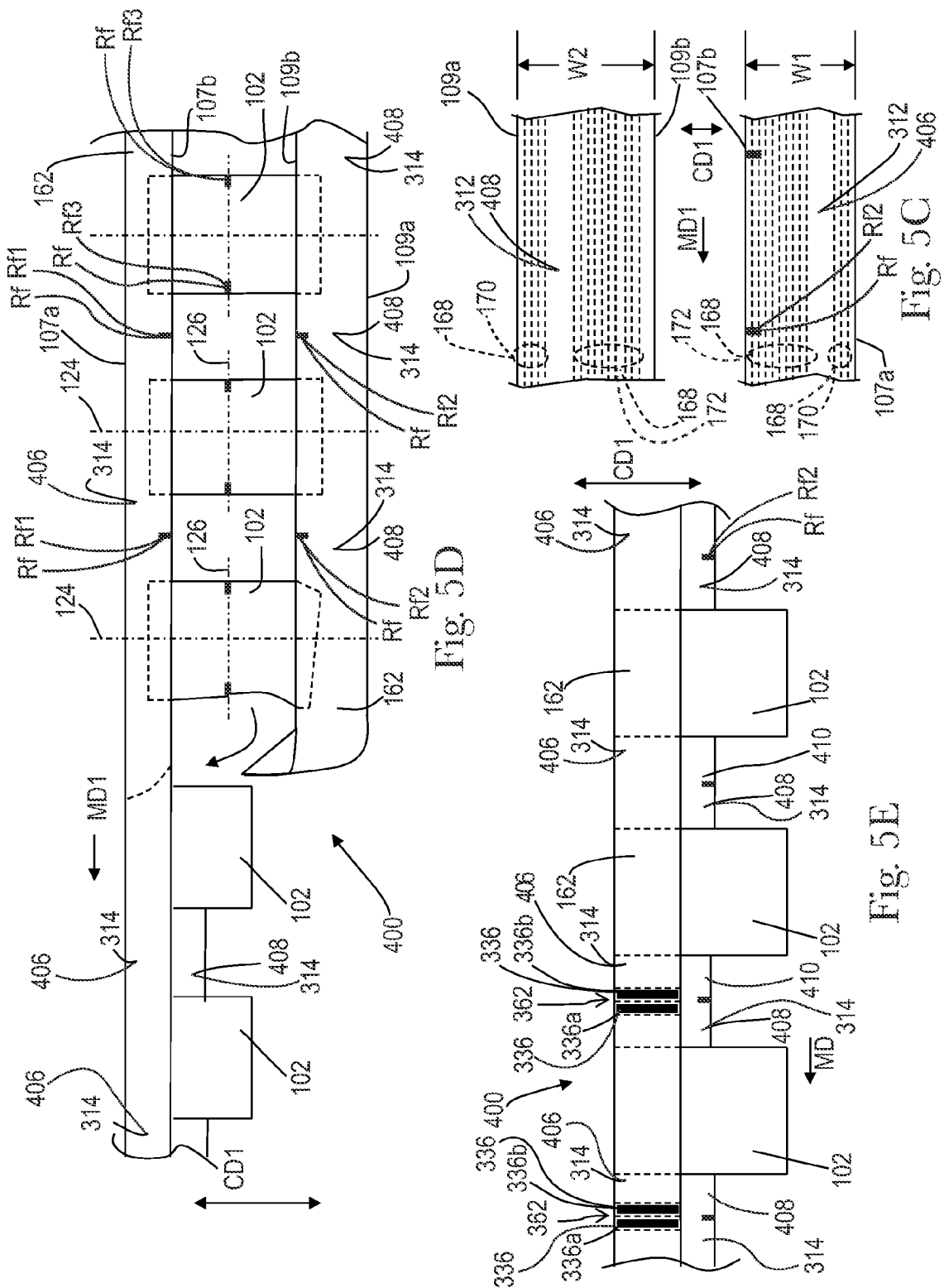

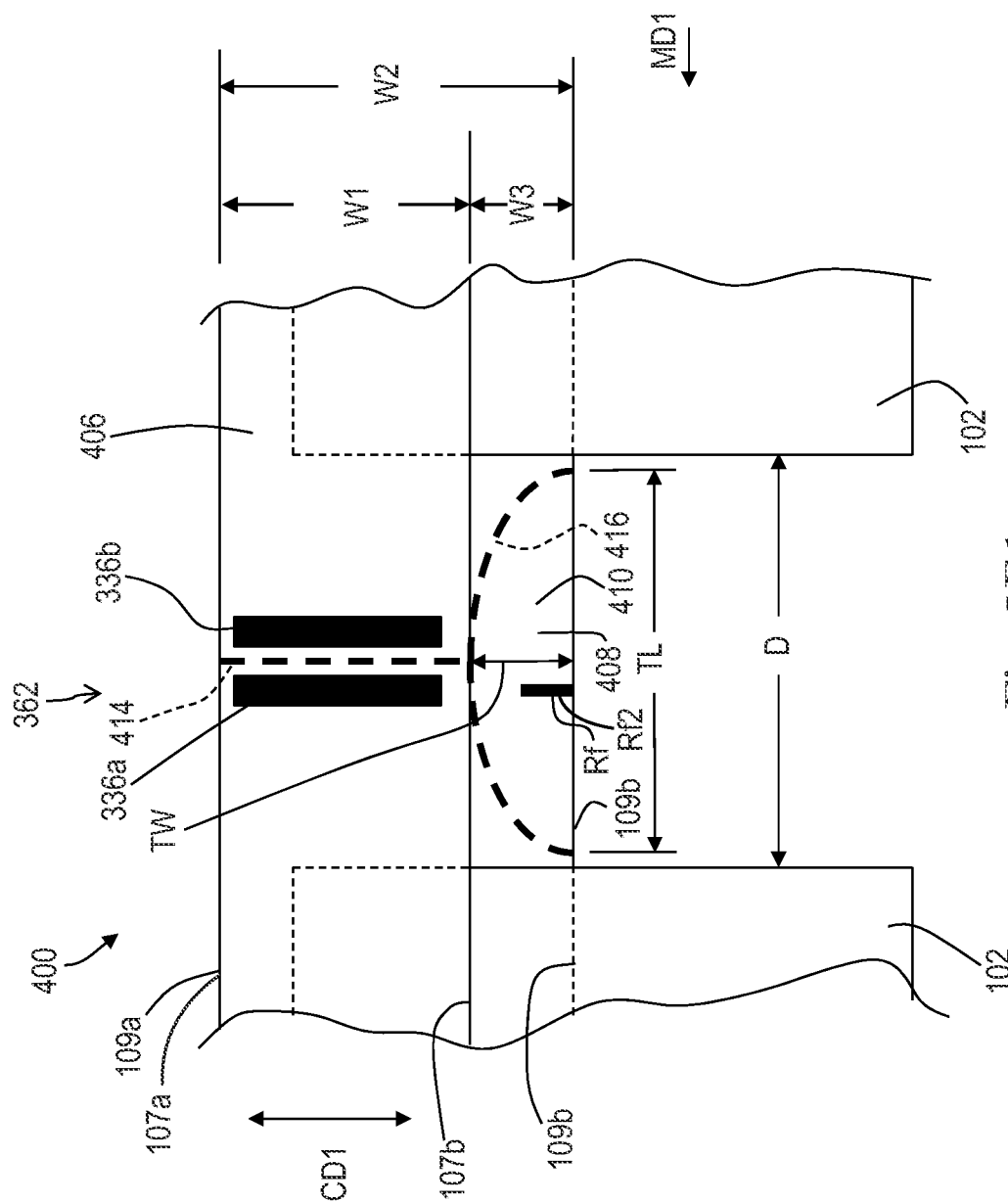

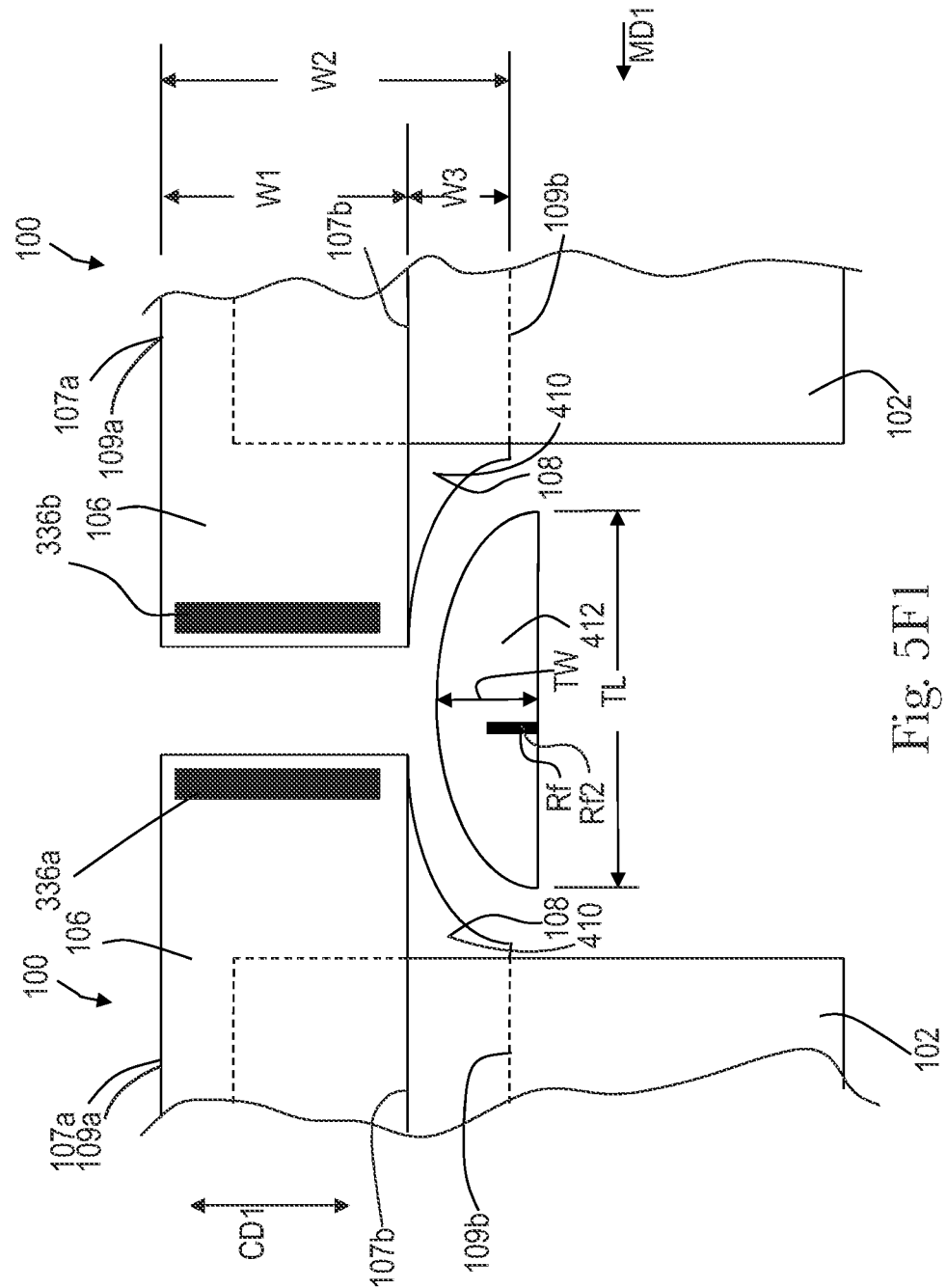
Fig. 5F1

APPARATUSES AND METHODS FOR MAKING ABSORBENT ARTICLES

CROSS REFERENCE TO RELATED APPLICATIONS

This application claims the benefit of U.S. Provisional Application No. 61/947,628, filed Mar. 4, 2014, which is herein incorporated by reference in its entirety.

FIELD OF THE INVENTION

The present disclosure relates to methods for manufacturing absorbent articles, and more particularly, to apparatuses and methods for controlling the registration of advancing substrates and discrete components in diaper converting lines.

BACKGROUND OF THE INVENTION

Along an assembly line, adding components to and/or otherwise modifying an advancing, continuous web of material may enable the assembly of various types of articles, such as for example, diapers and other absorbent articles. For example, in some processes, advancing webs of material are combined with other advancing webs of material. In other examples, individual components created from advancing webs of material are combined with advancing webs of material, which in turn, are then combined with other advancing webs of material. In some cases, individual components created from advancing web or webs are combined with other individual components created from other advancing web or webs. Webs of material and component parts used to manufacture diapers may include: backsheets, topsheets, leg cuffs, waist bands, absorbent core components, front and/or back belts or ears, fastening components, and various types of elastic webs and components such as leg elastics, barrier leg cuff elastics, stretch side panels, belts, and waist elastics. Once the desired component parts are assembled, the advancing web(s) and component parts are subjected to a final knife cut to separate the web(s) into discrete diapers or other absorbent articles.

Some diaper pant embodiments are configured with a chassis connected with front and back elastic belts, wherein laterally opposing end regions of the front and back belts are connected with each other at side seams. In some process configurations adapted to assemble such diaper pants, stretched elastic strands are glued between two continuous nonwoven webs to form a continuous elastic laminate. The continuous elastic laminate may be subsequently cut along the machine direction to form two separate continuous elastic laminates, which are adapted to form the front and back elastic belts. Next, discrete chassis may be bonded with the continuous elastic laminates; the chassis may be folded; and the elastic laminates may be bonded to each other and subjected to a final knife cut.

However, in some converting operations, the discrete chassis may be cut from an advancing continuous laminate; subsequently turned 90 degrees; and accelerated or decelerated before being combined with the advancing elastic laminates. Such manufacturing processes require control of the placement and combination of the chassis with the advancing elastic laminates in both machine and cross directions in order to control the relative positions of these components in a desired manner Consequently, it would be beneficial to provide methods and apparatuses that are configured to provide relatively precise registration processes and web handling systems to combine the chassis with the advancing elastic laminates in such a way to maximize the aesthetic appearances of assembled products.

SUMMARY OF THE INVENTION

The present disclosure relates to methods and apparatuses for controlling the relative placement of advancing substrates and discrete components in diaper converting lines. The diapers may each include a chassis connected with front and back elastic belts. In controlling the relative placement of these elements during the assembly process, a controller may change the machine direction speed and/or position of certain elements and cross direction speed and/or position of other elements such as the advancing substrates and components in order to help achieve proper placement and orientation. During the assembly process, the registration features are detected, and a controller may change the machine direction speeds of the advancing elastic laminates and/or chassis and/or may change the cross directional and/or machine direction position of the advancing elastic laminates and/or chassis.

In one embodiment, a method for assembling disposable pant diapers, wherein each pant diaper includes a chassis having a first end region and an opposing second end region separated from each other by a central region, and having a longitudinal axis and a lateral axis, the chassis comprising: a topsheet, a backsheet, and an absorbent core disposed between the topsheet and the backsheet, includes the steps of: advancing a first continuous substrate in a first machine direction at a first speed, the first continuous substrate defining a width in a first cross direction, wherein the first continuous substrate includes first registration features arranged along the first machine direction; advancing a second continuous substrate in a second machine direction at a second speed, the second continuous substrate defining a width in a second cross direction, wherein the second continuous substrate includes second registration features arranged along the second machine direction; cutting the second continuous substrate into discrete chassis, wherein each chassis advances such that the longitudinal axis is parallel with the second machine direction; turning each chassis such that the lateral axis is parallel with the first machine direction; bonding the first end regions of each chassis with the first continuous substrate; detecting positions of first and second registration features relative to each other along the first machine direction and along the first cross direction; changing placement of first and second registration features relative to each other along the first machine direction for each chassis subsequently bonded to the first continuous substrate based on detections of first and second registration features relative to each other on chassis previously bonded to the first continuous substrate by at least one of: adjusting the first speed of the first continuous substrate and shifting the second continuous substrate in the second cross direction; and changing the placement of first and second registration features relative to each other along the first cross direction for each chassis subsequently bonded to the first continuous substrate based on detections of first and second registration features relative to each other on chassis previously bonded to the first continuous substrate by at least one of: shifting the first continuous substrate in the first cross direction and adjusting the second speed of the second continuous substrate in the second machine direction.

In another embodiment, a method for assembling disposable pant diapers, wherein each pant diaper comprising a chassis having a first end region and an opposing second end region separated from each other by a central region, and having a longitudinal axis and a lateral axis, the chassis comprising: a topsheet, a backsheet, and an absorbent core disposed between the topsheet and the backsheet, includes the steps of: advancing a first continuous elastic laminate in a first machine direction at a first speed, the first continuous elastic laminate defining a width in a first cross direction, wherein the first continuous elastic laminate includes first registration features arranged along the first machine direction; advancing a second continuous elastic laminate in a second machine direction at a second speed, the second continuous elastic laminate defining a width in a second cross direction, wherein the second continuous elastic laminate includes second registration features arranged along the second machine direction; cutting the second continuous elastic laminate into discrete chassis, wherein each chassis advances such that the longitudinal axis is parallel with the second machine direction; turning each chassis such that the lateral axis is parallel with the first machine direction; bonding the first end regions of each chassis with the first continuous elastic laminate; advancing a third continuous elastic laminate in the first machine direction, the third continuous elastic laminate defining a width in the first cross direction, wherein the third continuous elastic laminate includes third registration features arranged along the first machine direction; and bonding the second end regions of each chassis with the third continuous elastic laminate; changing positions of the first, second, and third registration features relative to each other along the first machine direction; and changing the positions of the first, second, and third registration features relative to each other along the first cross direction.

In yet another embodiment, a method for assembling disposable pant diapers, wherein each pant diaper includes a chassis having a first end region and an opposing second end region separated from each other by a central region, and having a longitudinal axis and a lateral axis, the chassis comprising: a topsheet, a backsheet, and an absorbent core disposed between the topsheet and the backsheet, includes the steps of: advancing a first continuous substrate in a first machine direction at a first speed, the first continuous substrate having an outer longitudinal edge and an inner longitudinal edge defining a width in a first cross direction, wherein the first continuous substrate includes first registration features arranged along the first machine direction; advancing a second continuous substrate in a second machine direction at a second speed, the second continuous substrate defining a width in a second cross direction, wherein the second continuous substrate includes second registration features arranged along the second machine direction; cutting the second continuous substrate into discrete chassis, wherein each chassis advances such that the longitudinal axis is parallel with the second machine direction; turning each chassis such that the lateral axis is parallel with the first machine direction; bonding the first end regions of each chassis with the first continuous substrate; advancing a third continuous substrate in the first machine direction, the third continuous substrate having an outer longitudinal edge and an inner longitudinal edge defining a width in the first cross direction; and bonding the second end regions of each chassis with the third continuous substrate; folding each chassis along the lateral axis to position the first continuous substrate into a facing relationship with the third continuous substrate and defining uncovered regions of the first continuous substrate intermittently spaced between the chassis along the first machine direction and having a width extending in the first cross direction defined by a distance extending between the inner longitudinal edge of the first continuous elastic laminate and the inner longitudinal edge of the third continuous elastic laminate; and removing at least portions of the first registration features by cutting discrete pieces of trim material from the uncovered regions of the first continuous substrate.

In still another embodiment, a method for assembling disposable pant diapers, wherein each pant diaper includes a chassis having a first end region and an opposing second end region separated from each other by a central region, and having a longitudinal axis and a lateral axis, the chassis comprising: a topsheet, a backsheet, and an absorbent core disposed between the topsheet and the backsheet, includes the steps of: advancing a first continuous substrate in a first machine direction at a first speed, the first continuous substrate defining a width in a first cross direction, wherein the first continuous substrate includes first registration features arranged along the first machine direction; advancing a second continuous substrate in a second machine direction at a second speed, the second continuous substrate defining a width in a second cross direction, wherein the second continuous substrate includes second registration features arranged along the second machine direction; cutting the second continuous substrate into discrete chassis, wherein each chassis advances such that the longitudinal axis is parallel with the second machine direction; turning each chassis such that the lateral axis is parallel with the first machine direction; detecting positions of first and second registration features relative to each other along the first machine direction and along the first cross direction; changing placement of first and second registration features relative to each other along the first machine direction for each chassis based on detections of first and second registration features relative to each other by at least one of: adjusting the first speed of the first continuous substrate and shifting the second continuous substrate in the second cross direction; changing placement of first and second registration features relative to each other along the first cross direction for each chassis based on detections of first and second registration features relative to each other by at least one of: shifting the first continuous substrate in the first cross direction and adjusting the second speed of the second continuous substrate in the second machine direction; and subsequently bonding the first end regions of each chassis with the first continuous substrate.

BRIEF DESCRIPTION OF THE DRAWINGS

FIG. 2A is a partially cut away plan view of the diaper pant shown in FIGS. 1A and 1B in a flat, uncontracted state.

FIG. 3A is a cross-sectional view of the diaper pant of FIG. 2A taken along line 3A-3A.

FIG. 3B is a cross-sectional view of the diaper pant of FIG. 2A taken along line 3B-3B.

FIG. 5A is a view of a continuous length of chassis assemblies from FIG. 4 taken along line A-A.

FIG. 5B1 is a view of a discrete chassis from FIG. 4 taken along line B1-B1.

FIG. 5B2 is a view of a discrete chassis from FIG. 4 taken along line B2-B2.

FIG. 5C is a view of continuous lengths of advancing front and back side panel material from FIG. 4 taken along line C-C.

FIG. 5D is a view of multiple discrete chassis spaced from each other along the machine direction MD and connected with each other by the front and back side panel material from FIG. 4 taken along line D-D.

FIG. 5E is a view of folded multiple discrete chassis with the front and back side panel material in a facing relationship from FIG. 4 taken along line E-E.

FIG. 5E1 is a detailed view of a bonded overlapped area from FIG. 5E.

FIG. 5F is a view of two discrete absorbent articles advancing the machine direction MD from FIG. 4 taken along line F-F.

FIG. 5F1 is a detailed view of a bonded overlapped area from FIG. 5F.

DETAILED DESCRIPTION OF THE INVENTION

Figure 1A:
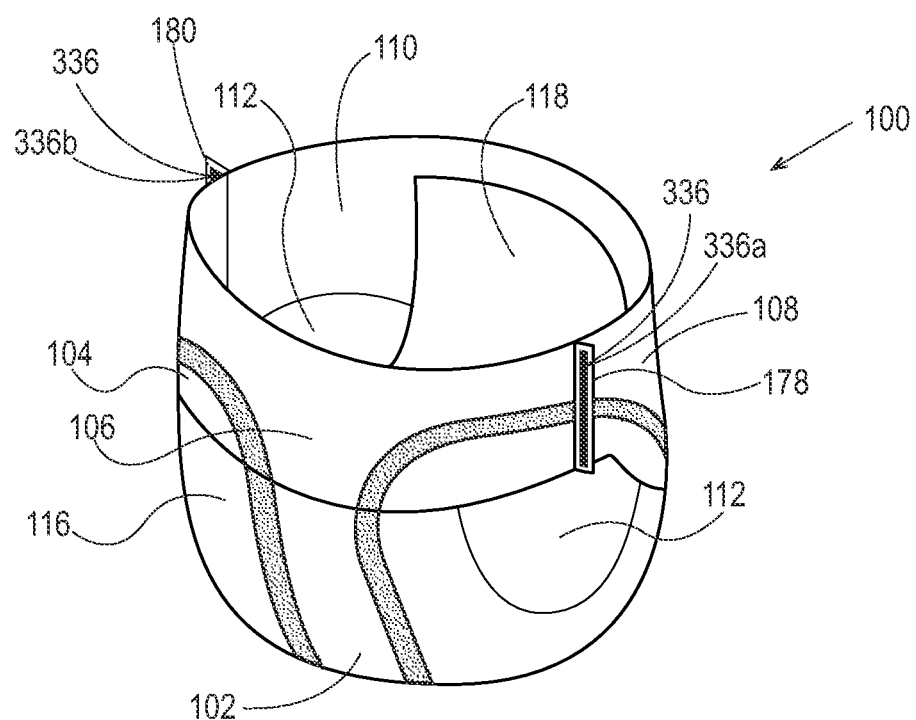
FIG. 1A is a front perspective view of a diaper pant.

The following term explanations may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

As used herein, the term "graphic" refers to images or designs that are constituted by a figure (e.g., a line(s)), a symbol or character, a color difference or transition of at least two colors, or the like. A graphic may include an aesthetic image or design that can provide certain benefit(s) when viewed. A graphic may be in the form of a photographic image. A graphic may also be in the form of a 1-dimensional (1-D) or 2-dimensional (2-D) bar code or a quick response (QR) bar code. A graphic design is determined by, for example, the color(s) used in the graphic (individual pure ink or spot colors as well as built process colors), the sizes of the entire graphic (or components of the graphic), the positions of the graphic (or components of the graphic), the movements of the graphic (or components of the graphic), the geometrical shapes of the graphic (or components of the graphics), the number of colors in the graphic, the variations of the color combinations in the graphic, the number of graphics printed, the disappearance of color(s) in the graphic, and the contents of text messages in the graphic.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

"Radial" means a direction running from the center of a drum toward a drum outer circumferential surface.

The term "substrate" is used herein to describe a material which is primarily two-dimensional (i.e. in an XY plane) and whose thickness (in a Z direction) is relatively small (i.e. $\frac{1}{10}$ or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed).

The present disclosure relates to methods and apparatuses for assembling absorbent articles, and in particular, to methods and apparatuses for controlling the relative placement of advancing substrates and discrete components in diaper converting lines. The diapers may each include a chassis connected with front and back elastic belts. The chassis may include a topsheet, a backsheet, and an absorbent core disposed between the topsheet and the backsheet. The chassis may also have a first end region and an opposing second end region separated from each other by a central region. During the assembly process, opposing end regions of the chassis are connected with the elastic belts in the form of first and second continuous elastic laminates. The chassis are then folded to place the elastic laminates into a facing relationship. Once the chassis are folded, the first and second continuous elastic laminates are cut in the cross direction to form discrete pant diapers. In controlling the relative placement of these elements during the assembly process, a controller may change the machine direction speed and/or position of certain elements and cross direction speed and/or position of other elements such as the advancing substrates and components in order to help achieve proper placement and orientation. The controller may affect such changes in speeds and positions based on the detection of registration features. In some configurations, the first and/or second elastic laminates and chassis may include registration features. During the assembly process, the registration features are detected, and a controller may change the machine direction speeds of the advancing elastic laminates and/or chassis and/or may change the cross directional and/or machine direction position of the advancing elastic laminates and/or chassis. It is to be appreciated that the speed changes discussed herein may be transient changes or steady step changes. With a transient change, an object or substrate advancing at a first speed may be temporarily accelerated or decelerated to a second speed, and then decelerated or accelerated back to the first speed. With steady step change, an object or substrate advancing at a first speed may be accelerated or decelerated to a second speed.

For example, as discussed below, a first continuous substrate, such as an elastic belt laminate, may advance in a first machine direction at a first speed, wherein the first continuous substrate defines a width in a first cross direction. The first continuous substrate includes first registration features arranged along the first machine direction. In addition, a second continuous substrate, such as a continuous length of chassis assemblies, may advance in a second machine direction at a second speed, wherein the second continuous substrate defines a width in a second cross direction. The second continuous substrate includes second registration features arranged along the second machine direction. The advancing second continuous substrate may then be cut into discrete chassis, wherein each chassis advances such that the longitudinal axis is parallel with the second machine direction. Each chassis may be turned such that the lateral axis is parallel with the first machine direction. While turning, the second speed of each chassis may also be altered to the first speed. Once turned, the first end regions of each chassis may be bonded with the first continuous substrate. Based on detections of the first and second registration features, a controller may then adjust the first speed of the first continuous substrate and/or the cross direction position of the first continuous substrate and a controller may adjust the speed of the second continuous substrate and/or shift the second continuous substrate in the second cross direction to change the relative positions of the first and second registration features along the first machine direction. In addition, a controller may alter the speed and/or shift the position of the discrete chassis relative to the first continuous substrate in the first cross direction and/or adjust the second speed of the second continuous substrate in the second machine direction to change the relative positions of the first and second registration features along the first cross direction, and thus, to bring the discrete chassis and the first continuous substrate into proper alignment.

Further to the above discussion, a third continuous substrate, such as an elastic belt laminate, may also advance in the first machine direction at a third speed, wherein the third continuous substrate defines a width in the first cross direction. And the second end regions of each chassis are bonded with the third continuous substrate. The third continuous substrate may also include third registration features arranged along the first machine direction. Thus, based on detections of the first, second, and third registration features, the controller may adjust the first speed of the first continuous substrate, the third speed of the third continuous substrate, and/or shift the second continuous substrate in the second cross direction to change the relative positions of the first, second, and third registration features along the first machine direction. In addition, the controller may shift the first and/or third continuous substrates in the first cross direction and/or adjust the second speed of the second continuous substrate in the second machine direction to change the relative positions of the first, second, and third registration features along the first cross direction. Further, each chassis may be folded along the lateral axis to position the first continuous substrate into a facing relationship with the third continuous substrate. And the first continuous substrate may be bonded with the third continuous substrate at discrete bond regions. The first and third continuous substrates may then be cut along the first cross direction to form discrete pant diapers.

It is to be appreciated that either first or third continuous substrates may be used to form either the front or back elastic belts. In some configurations, the first continuous substrate may include registration features, and the third continuous substrate may not include registration features. In addition, the first continuous substrate may be used to form the back elastic belt, and the third continuous substrate may be used to form the front elastic belt. And the registration features may be subsequently removed from the first continuous substrate. In some configurations, the registration features may be simultaneously removed from the first continuous substrate while the first and third continuous elastic laminates are cut along the first cross direction to form discrete pant diapers.

As discussed in more detail below, graphics or portions of graphics on various substrates may be relatively consistently positioned relative to the registration features. Thus, adjustments of the relative positions of the registration features during the assembly process may be used to combine the chassis with the advancing elastic laminates in such a way to maximize the aesthetic appearances of the graphics on assembled products. For example, the front and/or back elastic belts as well as the chassis may include graphics. And some graphics may be configured to appear as a design that appears to extend contiguously across combined diaper components, such as the front elastic belt, chassis, and/or back elastic belt. Thus, in some converting configurations, continuous nonwoven webs used to form the elastic laminates may include portions of such graphics. And some chassis components, such as a backsheet or topsheet, may include portions of such graphics. Therefore, during the assembly process, the chassis and elastic laminates may be assembled such that the graphic portions are combined to provide the appearance of contiguous designs that extend across more than one component, such as the elastic laminates and/or chassis.

As previously mentioned, the processes and apparatuses discussed herein may be used in the manufacture of different types of absorbent articles. To help provide additional context to the subsequent discussion of the process embodiments, the following provides a general description of absorbent articles in the form of diaper pants that include belt substrates that may be cut in accordance with the methods and apparatuses disclosed herein.

Figure 1B:
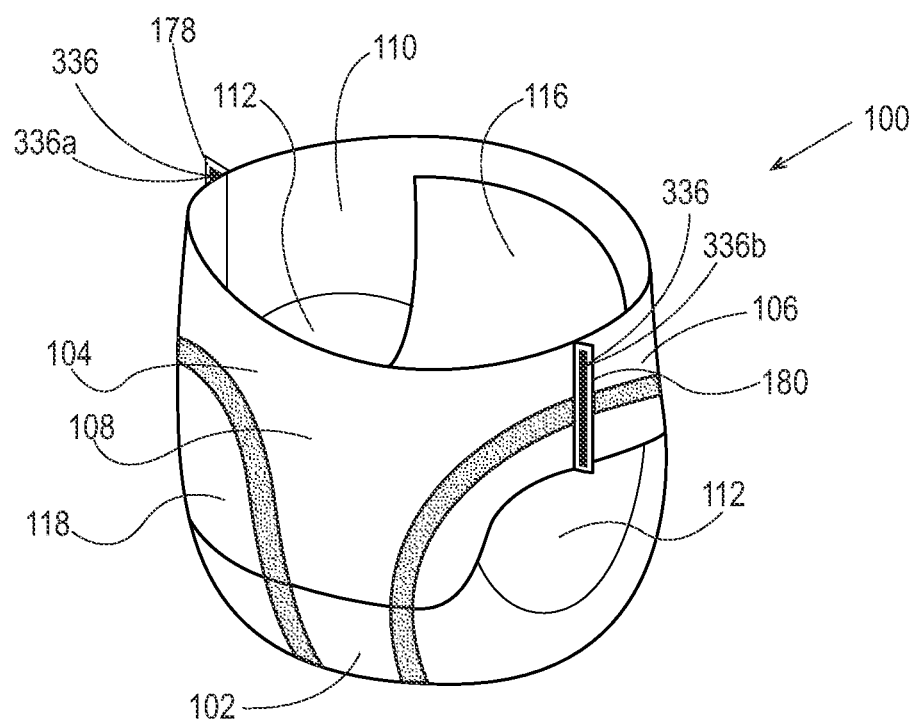
FIG. 1B is a rear perspective view of a diaper pant.
Figure 2B:
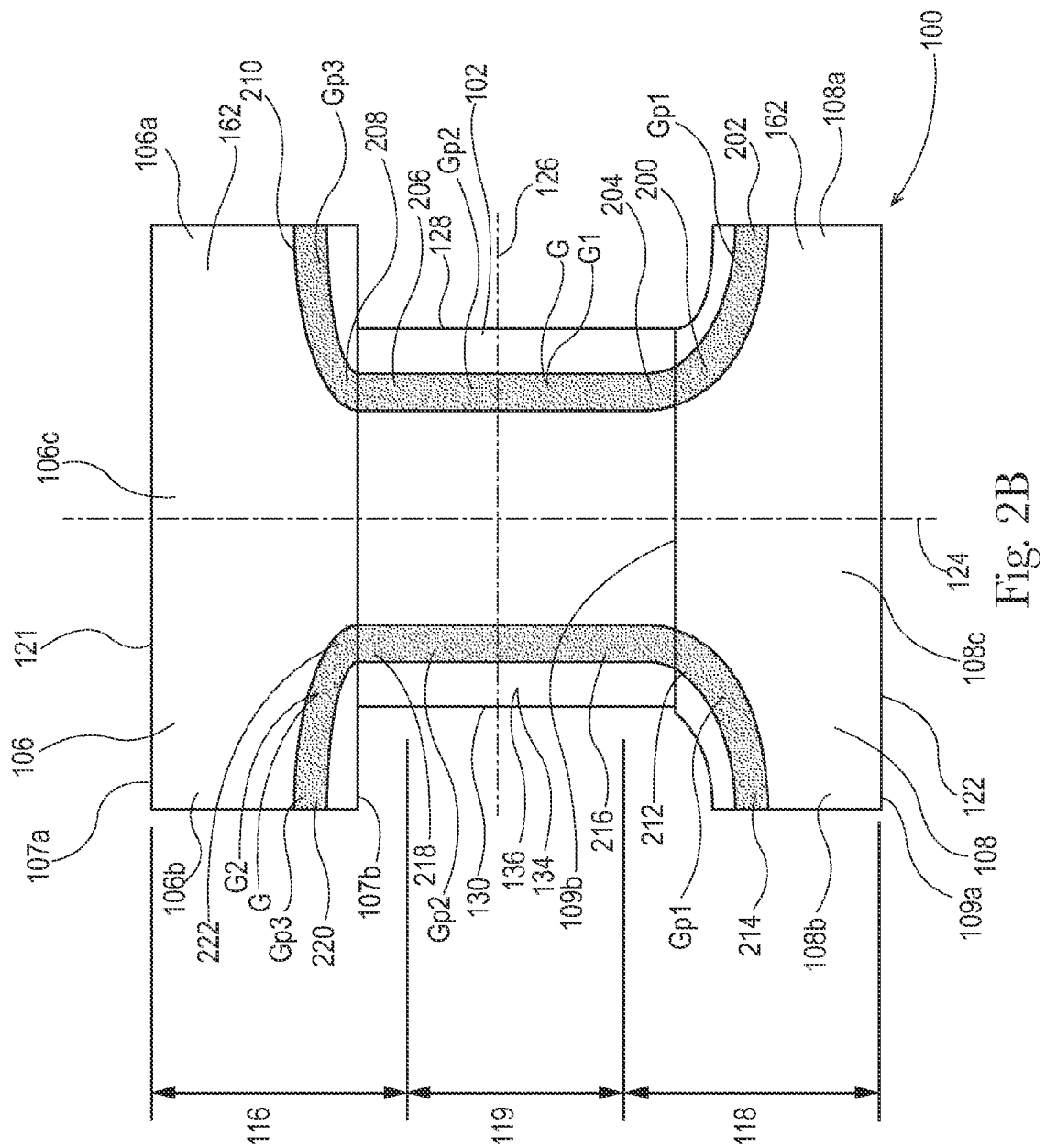
FIG. 2B is a plan view of the diaper pant shown in FIGS. 1A and 1B in a flat, uncontracted state.

FIGS. 1A, 1B, 2A, and 2B show an example of a diaper pant 100 that may be assembled and folded in accordance with the apparatuses and methods disclosed herein. In particular, FIGS. 1A and 1B show perspective views of a diaper pant 100 in a pre-fastened configuration, and FIGS. 2A and 2B show plan views of the diaper pant 100 with the portion of the diaper that faces away from a wearer oriented toward the viewer. The diaper pant 100 includes a chassis 102 and a ring-like elastic belt 104. As discussed below in more detail, a first elastic belt 106 and a second elastic belt 108 are bonded together to form the ring-like elastic belt 104. Although only the second elastic belt 108 is shown with a contoured or shaped edge, it is to be appreciated that either or both the first elastic belt 106 and second elastic belt 108 may include shaped edges made in accordance with the apparatuses and processes herein.

With continued reference to FIGS. 2A and 2B, the chassis 102 includes a first waist region 116, a second waist region 118, and a crotch region 119 disposed intermediate the first and second waist regions. The first waist region 116 may be configured as a front waist region, and the second waist region 118 may be configured as back waist region. In some embodiments, the length of each of the front waist region, back waist region, and crotch region may be ⅓ of the length of the absorbent article 100. The diaper 100 may also include a laterally extending front waist edge 121 in the front waist region 116 and a longitudinally opposing and laterally extending back waist edge 122 in the back waist region 118. To provide a frame of reference for the present discussion, the diaper 100 and chassis 102 of FIGS. 2A and 2B are shown with a longitudinal axis 124 and a lateral axis 126. In some embodiments, the longitudinal axis 124 may extend through the front waist edge 121 and through the back waist edge 122. And the lateral axis 126 may extend through a first longitudinal or right side edge 128 and through a midpoint of a second longitudinal or left side edge 130 of the chassis 102.

As shown in FIGS. 1A, 1B, 2A, and 2B, the diaper pant 100 may include an inner, body facing surface 132, and an outer, garment facing surface 134. The chassis 102 may include a backsheet 136 and a topsheet 138. The chassis 102 may also include an absorbent assembly 140, including an absorbent core 142, disposed between a portion of the topsheet 138 and the backsheet 136. As discussed in more detail below, the diaper 100 may also include other features, such as leg elastics and/or leg cuffs to enhance the fit around the legs of the wearer.

As shown in FIGS. 2A and 2B, the periphery of the chassis 102 may be defined by the first longitudinal side edge 128, a second longitudinal side edge 130, a first laterally extending end edge 144 disposed in the first waist region 116, and a second laterally extending end edge 146 disposed in the second waist region 118. Both side edges 128 and 130 extend longitudinally between the first end edge 144 and the second end edge 146. As shown in FIG. 2A, the laterally extending end edges 144 and 146 are located longitudinally inward from the laterally extending front waist edge 121 in the front waist region 116 and the laterally extending back waist edge 122 in the back waist region 118.

When the diaper pant 100 is worn on the lower torso of a wearer, the front waist edge 121 and the back waist edge 122 of the chassis 102 may encircle a portion of the waist of the wearer. At the same time, the chassis side edges 128 and 130 may encircle at least a portion of the legs of the wearer. And the crotch region 119 may be generally positioned between the legs of the wearer with the absorbent core 142 extending from the front waist region 116 through the crotch region 119 to the back waist region 118.

It is to also be appreciated that a portion or the whole of the diaper 100 may also be made laterally extensible. The additional extensibility may help allow the diaper 100 to conform to the body of a wearer during movement by the wearer. The additional extensibility may also help, for example, the user of the diaper 100, including a chassis 102 having a particular size before extension, to extend the front waist region 116, the back waist region 118, or both waist regions of the diaper 100 and/or chassis 102 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the diaper pant 100 may include a backsheet 136. The backsheet 136 may also define the outer surface 134 of the chassis 102. The backsheet 136 may be impervious to fluids (e.g., menses, urine, and/or runny feces) and may be manufactured in part from a thin plastic film, although other flexible liquid impervious materials may also be used. The backsheet 136 may prevent the exudates absorbed and contained in the absorbent core from wetting articles which contact the diaper 100, such as bedsheets, pajamas and undergarments. The backsheet 136 may also comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also comprise an elastomeric film. An example backsheet 136 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte-finished to provide a more clothlike appearance. Further, the backsheet 136 may permit vapors to escape from the absorbent core (i.e., the backsheet is breathable) while still preventing exudates from passing through the backsheet 136. The size of the backsheet 136 may be dictated by the size of the absorbent core 142 and/or particular configuration or size of the diaper 100.

Also described above, the diaper pant 100 may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art.

Topsheets 138 may be selected from high loft nonwoven topsheets, apertured film topsheets and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916,661; 6,545,197; and 6,107,539.

As mentioned above, the diaper pant 100 may also include an absorbent assembly 140 that is joined to the chassis 102. As shown in FIG. 2A, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprises primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 and 2004/0097895.

As previously mentioned, the diaper 100 may also include elasticized leg cuffs 156. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695,278; 4,795,454; 4,704,115; 4,909,803; and U.S. Patent Publication No. 2009/0312730A1.

As mentioned above, diaper pants may be manufactured with a ring-like elastic belt 104 and provided to consumers in a configuration wherein the front waist region 116 and the back waist region 118 are connected to each other as packaged, prior to being applied to the wearer. As such, diaper pants may have a continuous perimeter waist opening 110 and continuous perimeter leg openings 112 such as shown in FIGS. 1A and 1B. The ring-like elastic belt may be formed by joining the first elastic belt to a second elastic belt with a permanent side seam or with an openable and reclosable fastening system disposed at or adjacent the laterally opposing sides of the belts.

As previously mentioned, the ring-like elastic belt 104 is defined by a first elastic belt 106 connected with a second elastic belt 108. As shown in FIG. 2A, the first elastic belt 106 defines first and second opposing end regions 106a, 106b and a central region 106c, and the second elastic 108 belt defines first and second opposing end regions 108a, 108b and a central region 108c. The central region 106c of the first elastic belt is connected with the first waist region 116 of the chassis 102, and the central region 108c of the second elastic belt 108 is connected with the second waist region 116 of the chassis 102. As shown in FIGS. 1A and 1B, the first end region 106a of the first elastic belt 106 is connected with the first end region 108a of the second elastic belt 108 at first side seam 178, and the second end region 106b of the first elastic belt 106 is connected with the second end region 108b of the second elastic belt 108 at second side seam 180 to define the ring-like elastic belt 104 as well as the waist opening 110 and leg openings 112.

As shown in FIGS. 2A, 3A, and 3B, the first elastic belt 106 also defines an outer laterally extending edge 107a and an inner laterally extending edge 107b, and the second elastic belt 108 defines an outer laterally extending edge 109a and an inner laterally extending edge 109b. The outer laterally extending edges 107a, 109a may also define the front waist edge 121 and the laterally extending back waist edge 122. The first elastic belt and the second elastic belt may also each include an outer, garment facing layer 162 and an inner, wearer facing layer 164. It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that the first elastic belt 106 and the second elastic belt 108 may be constructed from various materials. For example, the first and second belts may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the first and second elastic belts include a nonwoven web of synthetic fibers, and may include a stretchable nonwoven. In other embodiments, the first and second elastic belts include an inner hydrophobic, non-stretchable nonwoven material and an outer hydrophobic, non-stretchable nonwoven material.

The first and second elastic belts 106, 108 may also each include belt elastic material interposed between the outer layer 162 and the inner layer 164. The belt elastic material may include one or more elastic elements such as strands, ribbons, films, or panels extending along the lengths of the elastic belts. As shown in FIGS. 2A, 3A, and 3B, the belt elastic material may include a plurality of elastic strands 168 which may be referred to herein as outer, waist elastics 170 and inner, waist elastics 172. Elastic strands 168, such as the outer waist elastics 170, may continuously extend laterally between the first and second opposing end regions 106a, 106b of the first elastic belt 106 and between the first and second opposing end regions 108a, 108b of the second elastic belt 108. In some embodiments, some elastic strands 168, such as the inner waist elastics 172, may be configured with discontinuities in areas, such as for example, where the first and second elastic belts 106, 108 overlap the absorbent assembly 140. In some embodiments, the elastic strands 168 may be disposed at a constant interval in the longitudinal direction. In other embodiments, the elastic strands 168 may be disposed at different intervals in the longitudinal direction. The belt elastic material in a stretched condition may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like elastic belt. It is to be appreciated that the chassis 102 and elastic belts 106, 108 may be configured in different ways other than as depicted in FIG. 2A. The belt elastic material may be joined to the outer and/or inner layers continuously or intermittently along the interface between the belt elastic material and the inner and/or outer belt layers.

In some configurations, the first elastic belt 106 and/or second elastic belt 108 may define curved contours. For example, as shown in FIG. 2A, the inner lateral edge 109b of the second elastic belt 108 may include non-linear or curved portions 109c in the first and second opposing end regions 108a, 108b. Such curved contours may help define desired shapes to leg opening 112, such as for example, relatively rounded leg openings. Although the inner lateral edge 107b of the first elastic belt is depicted as being a straight line, it is to be appreciated that the inner lateral edge 107b may also include curved portions in the first and second opposing end regions 106a, 106b. In addition to having curved contours, the elastic belts 106, 108 may include elastic strands 168, 172 that extend along non-linear or curved paths that may correspond with the curved contours of the inner lateral edges 107b, 109b.

As previously mentioned, the diaper pant may include one or more graphics. For example, as shown in FIGS. 1A, 1B, and 2B, the diaper pant 100 may include graphics, G, represented by a first printed stripe G1 and/or a second printed stripe G2, each extending through the first waist region 116, the crotch region 119, and the second waist region 118. As shown in FIG. 2B, the first stripe G1 and the second stripe G2 each include a first portion Gp1, a second portion Gp2, and a third portion Gp3. In particular, the first portion Gp1 of each stripe G1, G2 may be located on the second elastic belt 108; the second portion Gp2 of each stripe G1, G2 may be located on the chassis 102; and the third portion Gp3 of each stripe G1, G2 may be located on the first elastic belt 106. As discussed in more detail below, aspects of the diaper converting process may be controlled such that the first elastic belt 106, second elastic belt 108, and chassis 102 are combined such that the first stripe G1 and/or second stripe G2 appear to be contiguous although each stripe includes multiple portions printed on different diaper components.

With reference to FIG. 2B, the first portion Gp1 of the first printed stripe G1 extends from a first end region 200 at the inner lateral edge 109b of the second elastic belt 108 to a second end region 202 at the first end region 108a of the second elastic belt 108. The second portion Gp2 of the first printed stripe G1 extends longitudinally through the crotch region 119 along the chassis 102 from a first end region 204 to a second end region 206. The third portion Gp3 of the first printed stripe G1 extends from a first end region 208 at the inner lateral edge 107b of the first elastic belt 106 to a second end region 210 at the first end region 106a of the first elastic belt 106. With continued reference to FIG. 2B, the first portion Gp1 of the second printed stripe G2 extends from a first end region 212 at the inner lateral edge 109b of the second elastic belt 108 to a second end region 214 at the second end region 108b of the second elastic belt 108. The second portion Gp2 of the second printed stripe G2 extends longitudinally through the crotch region 119 along the chassis 102 from a first end region 216 to a second end region 218. The third portion Gp3 of the second printed stripe G2 extends from a first end region 220 at the inner lateral edge 107b of the first elastic belt 106 to a second end region 222 at the second end region 106b of the first elastic belt 106.

It is to be appreciated that the second portion Gp2 of the first printed stripe G1 and/or second printed stripe G2 may define various lengths on the chassis 102. For example, the second portion Gp2 of the first and/or second printed stripes G1, G2 may extend along the entire length of the chassis 102 from the first laterally extending end edge 144 to the second laterally extending end edge 146. And as such, opposing end portions of the second portion Gp2 of the first and/or second printed stripes G1, G2 may be covered by the first and second elastic belts 106, 108. In other examples, the second portion Gp2 of the first and/or second printed stripes G1, G2 may extend less than the entire length of the chassis 102.

Figure 4:
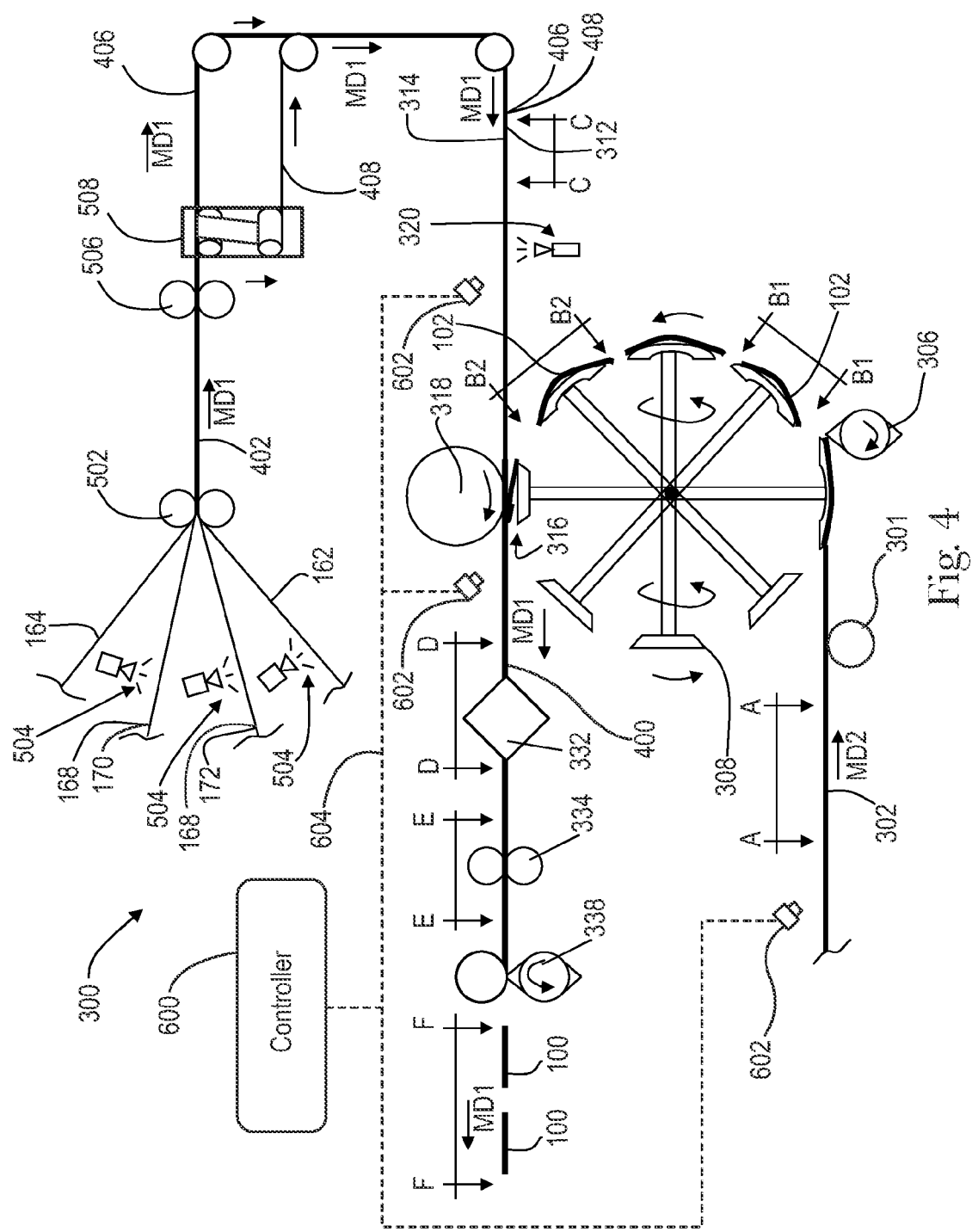
FIG. 4 is a schematic side view of a converting apparatus adapted to manufacture pre-fastened, pant diapers.

As previously mentioned, the apparatuses and methods according to the present disclosure may be utilized to assemble various components of pre-fastened, refastenable pant diapers 100. For example, FIG. 4 shows a schematic view of a converting apparatus 300 adapted to manufacture pant diapers 100. The method of operation of the converting apparatus 300 may be described with reference to the various components of pant diapers 100 described above and shown in FIGS. 1A, 1B, 2A, and 2B. Although the following methods are provided in the context of the diaper 100 shown in FIGS. 1A, 1B, 2A, and 2B, it is to be appreciated that various embodiments of diaper pants can be manufactured according to the methods disclosed herein, such as for example, the absorbent articles disclosed in U.S. Pat. No. 7,569,039; U.S. Patent Publication Nos. 2005/0107764A1, 2012/0061016A1, and 2012/0061015A1, which are all hereby incorporated by reference herein.

As described in more detail below, the converting apparatus 300 shown in FIG. 4 operates to advance first and second elastic belt laminates 406, 408 along a first machine direction MD1. In addition, a continuous length of chassis assemblies 302 are advanced in a second machine direction MD2 and cut into discrete chassis 102 such that the longitudinal axis of each chassis 102 is parallel with the second machine direction MD2. The discrete chassis 102 are then turned to advance the discrete chassis 102 along the first machine direction MD1 such that the lateral axis of each chassis 102 is parallel with the first machine direction MD1. The discrete chassis 102 are also spaced apart from each other along the first machine direction MD1. Opposing waist regions 116, 118 of the spaced apart chassis 102 are then connected with continuous lengths of advancing first and second elastic belt laminates 406, 408. The chassis 102 may then be folded along the lateral axis, or parallel to the lateral axis, to bring the first and second elastic belt laminates 406, 408 into a facing relationship, and the first and second elastic belt laminates are bonded together with laterally opposing bonds 336. As discussed in more detail below, the first and second elastic belt laminates may be bonded together with adjacent bonds 336a, 336b intermittently spaced along the first machine direction MD1. Each bond 336a, 336b may be a discrete bond site extending contiguously in a first cross direction CD1 across a width of the first and second elastic belt laminates and/or may include a plurality of relatively small, discrete bond sites arranged in the cross direction. The first and second continuous elastic laminates 406, 408 are then cut in the first cross direction CD1 between adjacent bonds 336a, 336b to create discrete pant diapers 100, such as shown in FIGS. 1A and 1B. In some configurations, discrete pieces of trim material may also be removed from regions of the first and/or second elastic belt laminates 406, 408 extending between adjacent folded chassis.

As shown in FIG. 4, a first continuous substrate layer in the form of a continuous length of outer layer belt material 162; a second continuous substrate layer in the form of a continuous length of inner layer belt material 164; and elastics 168 are combined to form a continuous elastic laminate in the form of a belt material 402. More particularly, continuous lengths of outer layer belt material 162, inner layer belt material 164, outer elastic strands 170 and inner elastic strands 172 are advanced in a first machine direction MD1 and combined at nip rolls 502 to form a continuous length of belt material 402. Before entering the nip rolls 502, the outer elastic strands 170 and inner elastic strands 172 are stretched in the first machine direction MD1. In addition, adhesive 504 may applied to the elastic strands 170, 172 as well as either or both of the continuous lengths of outer layer belt material 162 and inner layer belt material 164 before entering nip rolls 502. Further, adhesive 504 may be applied intermittently along the lengths of the inner elastic strands 172 and/or intermittently along the length of either or both of the continuous lengths of outer layer belt material 162 and inner layer belt material 164 before entering nip rolls 502. As such, the inner elastic strands 172 may be intermittently bonded to either or both of the continuous lengths of outer layer belt material 162 and inner layer belt material 164 along the first machine direction MD1. Thus, the belt material 402 may include non-bonded regions intermittently spaced between bonded regions along the first machine direction MD1, wherein the inner elastic strands 172 are not bonded to either the outer layer belt material 162 or inner layer belt material 164 in the non-bonded regions. And the inner elastic strands 172 are bonded to the outer layer belt material 162 and/or inner layer belt material 164 in the bonded regions. Although FIG. 4 shows an embodiment wherein the belt material 402 is formed by combining continuous lengths of outer layer belt material 162 and inner layer belt material 164 with elastics 168, it is to be appreciated the belt material 402 can be formed in various ways, such as disclosed in U.S. Pat. No. 8,440,043 and U.S. Patent Publication Nos. US2013/0255861A1; US2013/0255862A1; US2013/0255863A1; US2013/0255864A1; and US2013/0255865A1.

Referring back to FIG. 4, from the nip rolls 502 the continuous length of belt material 402 advances in the first machine direction MD1 to a cutter 506 that cuts the belt material 402 into two continuous belt substrates, referred to as a first belt substrate 406 and a second belt substrate 408. The cutter 506 may be configured in various ways. For example, in some embodiments the cutter 506 may be a slitter or a die cutter that separates the belt material into two continuous belt substrates with either a straight line cut and/or a curved line cut. The cutter 506 may also be configured as a perforator that perforates the belt material with a line of weakness and wherein the belt material is separated along the line of weakness in a later step. From the cutter 506, the first and second belt substrates 406, 408 advance through a diverter 508 that separates the first and second belt substrates from each other in the first cross direction CD1, such as shown in FIG. 5C. The elastic strands 170, 172, and thus, the continuous length of first and second belt substrates 406, 408 are maintained in a stretched condition while advancing along the first machine direction MD1. It is to be appreciated that the diverter 508 may be configured in various ways. For example, in some embodiments, the diverter 508 may include turn bars angled at 45 degrees or some other angle with respect to the machine direction. In some embodiments, the diverter may include cambered rollers. It is to be appreciated that the front and back belts may be formed by separate continuous lengths of belt material similar to the description above and as such would not required the slitting step or the diverting step.

In some embodiments, the diverter 508 may include a pivot or tracking table, such as for example, the FIFE-500 Web Guiding System, by Maxcess-FIFE Corporation, which can adjust the positions of the continuous length of first and second belt substrates 406, 408 in the first cross direction CD1. Other suitable pivot or tracking tables are available from Erhardt & Leimer, Inc. The diverter may also include instrumentation and web edge control features that allow for precise active control of the substrate positions.

As shown in FIG. 5C, the first belt substrate 406 includes an outer longitudinal edge 107a and an inner longitudinal edge 107b defining a substantially constant width, W1, in the first cross direction CD1. And the second belt substrate 408 includes an outer longitudinal edge 109a and an inner longitudinal edge 109b defining a substantially constant width, W2, in the first cross direction CD1, wherein W2 is greater than W1. It is to be appreciated that in some configurations, W1 may be equal to or greater than W2. As previously mentioned, the first belt substrate 406 is separated in the first cross direction from the second belt substrate 408 to define a gap between the inner longitudinal edge 107b of the first belt substrate 406 and the inner longitudinal edge 109b of the second belt substrate 408. As discussed in more detail below, the first and second belt substrates 406, 408 advance from the diverter 508 to a nip 316 between the carrier apparatus 308 and a carrier apparatus 318 to be combined with discrete chassis 102.

As shown in FIGS. 4 and 5A, a continuous length of chassis assemblies 302 are advanced in a second machine direction MD2 and define a width in a second cross direction CD2. The continuous length of chassis assemblies 302 may include absorbent assemblies 140 sandwiched between topsheet material 138 and backsheet material 136, leg elastics, barrier leg cuffs and the like. As shown in FIG. 5A, portion of the chassis assembly is cut-away to show a portion of the topsheet material 138 and an absorbent assembly 140. The continuous length of chassis assemblies 302 advance to a carrier apparatus 308 and are cut into discrete chassis 102 with knife roll 306, while advancing in the orientation shown in FIG. 5B1, wherein the longitudinal axis 124 of each chassis 102 is generally parallel with the second machine direction MD2.

In some embodiments, the converting apparatus 300 may include a pivot or tracking table 301, such as for example, the FIFE-500 Web Guiding System, by Maxcess-FIFE Corporation, which can adjust the positions of the continuous length of chassis assemblies 302 in the second cross direction CD2. Other suitable pivot or tracking tables are available from Erhardt & Leimer, Inc.

After the discrete absorbent chassis 102 are cut by the knife roll 306, the carrier apparatus 308 rotates and advances the discrete chassis 102 in the second machine direction MD2 in the orientation shown in FIG. 5B1. While the chassis 102 shown in FIG. 5B1 is shown with the second laterally extending end edge 146 as a leading edge and the first laterally extending end edge 144 as the trailing edge, it is to be appreciated that in other embodiments, the chassis 102 may be advanced in other orientations. For example, the chassis may be oriented such that the second laterally extending end edge 146 is a trailing edge and the first laterally extending end edge 144 is a leading edge. The carrier apparatus 308 also rotates while at the same time changing the orientation of the advancing chassis 102. In changing the chassis orientation, the carrier apparatus 308 may turn each chassis 102 such that the lateral axis 126 of the chassis 102 is parallel or generally parallel with the first machine direction MD1, such as shown in FIG. 5B2. The carrier apparatus 308 may also change the speed at which the chassis 102 advances in the second machine direction MD2 to a different speed in the first machine direction MD1. FIG. 5B2 shows the orientation of the chassis 102 on the carrier apparatus 308 while advancing in the first machine direction MD1. More particularly, FIG. 5B2 shows the chassis 102 with the lateral axis 126 of the chassis 102 generally parallel with the first machine direction MD1, and wherein the second longitudinal side edge 130 is the leading edge and the first longitudinal side edge 128 is the trailing edge. It is to be appreciated that various forms of carrier apparatuses may be used with the methods herein, such as for example, the carrier apparatuses disclosed in U.S. Pat. No. 7,587,966 and U.S. Patent Publication Nos. US2013/0270065A1; US2013/0270069A1; US20130270066A1; and US20130270067A1. As discussed below, in some embodiments, the carrier apparatus 308 may rotate at a variable angular velocity that may be changed or adjusted by a controller in order to change the relative placement of registration features on the chassis 102 and the advancing belt laminates 406, 408.

As discussed below with reference to FIGS. 4, 5C, 5D, 5E, and 5F, the chassis 102 are transferred from the carrier apparatus 308 and combined with advancing, continuous lengths of belt laminates 406, 408, which are subsequently cut to form first and second elastic belts 106, 108 on diapers 100.

With reference to FIGS. 4, 5C, and 5D, the chassis 102 are transferred from the carrier apparatus 308 to a nip 316 between the carrier apparatus 308 and a carrier apparatus 318 where the chassis 102 is combined with continuous lengths of advancing front belt 406 and back belt 408 substrate material. The front belt laminate material 406 and the back belt laminate material 408 each define a wearer facing surface 312 and an opposing garment facing surface 314. The wearer facing surface 312 of the first belt laminate 406 may be combined with the garment facing surface 134 of the chassis 102 along the first waist region 116, and the wearer facing surface 312 of the second belt laminate 408 may be combined with the garment facing surface 134 of the chassis 102 along the second waist region 118. As shown in FIG. 4, adhesive 320 may be intermittently applied to the wearer facing surface 312 of the first and second belt laminates 406, 408 before combining with the discrete chassis 102 at the nip 316 between roll 318 and the carrier apparatus 308.

With reference to FIGS. 4 and 5D, a continuous length of absorbent articles 400 are defined by multiple discrete chassis 102 spaced from each other along the first machine direction MD1 and connected with each other by the second belt laminate 408 and the first belt laminate 406. As shown in FIG. 4, the continuous length of absorbent articles 400 advances from the nip 316 to a folding apparatus 332. At the folding apparatus 332, each chassis 102 is folded in the first cross direction CD1 parallel to or along a lateral axis 126 to place the first waist region 116, and specifically, the inner, body facing surface 132 into a facing, surface to surface orientation with the inner, body surface 132 of the second waist region 118. The folding of the chassis also positions the wearer facing surface 312 of the second belt laminate 408 extending between each chassis 102 in a facing relationship with the wearer facing surface 312 of the first belt laminate 406 extending between each chassis 102. As shown in FIGS. 4, 5D, and 5E, the folded discrete chassis 102 connected with the first and second belt laminates 406, 408 are advanced from the folding apparatus 332 to a bonder apparatus 334. The bonder apparatus 334 operates to bond an overlap area 362, thus creating discrete bonds 336a, 336b. The overlap area 362 includes a portion of the second belt laminate 408 extending between each chassis 102 and a portion of the first belt laminate 406 extending between each chassis 102.

As previously mentioned, the first belt laminate 406 may define a first width, W1, in the first cross direction CD1 and the second belt laminate may define a second width, W2, in the first cross direction CD1, wherein W2 is greater than W1. Thus, as shown in FIGS. 5E and 5E1, folding each chassis 102 and positioning the first belt laminate 406 into a facing relationship with the second belt laminate 408 may define uncovered regions 410 of the second belt laminate 408 intermittently spaced between the chassis 102 along the first machine direction MD1. The uncovered regions 410 may have a width, W3, extending in the cross direction defined by a distance extending between the inner longitudinal edge 107b of the first belt laminate 406 and the inner longitudinal edge 109b of the second belt laminate 408. It is to be appreciated that folding each chassis 102 and positioning the first belt laminate 406 into a facing relationship with the second belt laminate 408 may also include aligning the outer longitudinal edge 107a of the first belt laminate 406 with the outer longitudinal edge 109a of the second belt laminate 408.

As shown in FIGS. 4 and 5F, the continuous length of absorbent articles 400 are advanced from the bonder 334 to a cutting apparatus 338 where the first belt laminate 406 and the second belt laminate 408 are cut along the first cross direction CD1 between adjacent bonds 336a, 336b to create discrete absorbent articles 100. As such, bond 336a may correspond with and form a first side seam 178 on an absorbent article 100, and the bond 336b may correspond with and form a second side seam 180 on a subsequently advancing absorbent article.

In addition to cutting the first belt laminate 406 and the second belt laminate 408 along the first cross direction CD1 between adjacent bonds 336a, 336b, the cutting apparatus 338 may also be configured to remove discrete pieces of trim material 412 from the uncovered regions 410 of the second belt laminate 408, such as shown in FIGS. 5E1 and 5F1. As shown in FIG. 5E1, the cutting apparatus 338 may be configured to cut the first and second belt laminates 406, 408 along a first cut line 414 and a second cut line 416. The first cut line 414 may extend in the first cross direction CD1 to sever the first and second belt laminates 406, 408. And the second cut line may extend in the first machine direction MD1 and first cross direction CD1 to sever the pieces of trim material 412 from the first belt laminate 406 and/or the second belt laminate 408. As such, the cutting apparatus 338 may be configured to cut discrete absorbent articles 100 from the continuous length of absorbent articles 400 while at the same time forming contoured and/or shaped front and/or back elastic belts 106, 108 on the absorbent articles 100. As discussed below, the processes and apparatuses herein may be configured to produce absorbent articles 100 having a front elastic belt 106 with a substantially constant width and a back elastic belt 108 having a variable width defined by a contoured or shaped edge 109*b*.

It is to be appreciated that the first and second cut lines may be configured in various ways. For example, as shown in FIGS. 5E1 and 5F1, the first cut line 414 may extend in a straight line in the first cross direction CD1 to intersect with the second cut line 416. The second cut line may extend in a curved path to define a length TL in the first machine direction MD1. As shown in FIG. 5E1, the adjacent chassis 102 may be separated from each other in the first machine direction MD1 by a distance D, and as such, the second cut line 416 may have a length TL that is equal to or less then the distance D such that the chassis 102 are not cut while removing the trim material 412. However, in some embodiments, the length TL may be greater than the distance D. The second cut line 416 may also intersect with and extend in the first cross direction CD1 from the inner longitudinal edge 107*b* and/or inner longitudinal edge 109*b* of the first and/or second belt laminates 406, 408. For example, as shown in FIG. 5E1, the second cut line 416 extends in the first cross direction CD1 from the inner longitudinal edge 109*b* of the second belt laminate 408 a distance TW to intersect with the first cut line 414. Thus, as shown in FIG. 5F1, the piece of trim material 412 may have a corresponding length TL and width TW.

It is to be appreciated that the first cut line 414 may extend along a straight and/or curved path along the first cross direction CD1. In addition, the first cut line 414 may be perpendicular with respect to the outer longitudinal edge 107*a* and/or outer longitudinal edge 109*a* of the first and/or second belt laminates 406, 408. In some configurations, the first cut line 414 may be define an angle that is less than 90° with respect to the outer longitudinal edge 107*a* and/or outer longitudinal edge 109*a*. In addition, it is to be appreciated that the second cut line 416 may extend along a path defined by straight and/or curved portions.

With continued reference to FIGS. 5E1 and 5F1, the cutting apparatus 338 may be configured to remove trim material 412 from only the uncovered regions 410 of the second belt laminate 408 without removing material from the first belt laminate 406. For example, the first cut line 414 may extend from the outer longitudinal edges 107*a*, 109*a* of the first and second belt laminates 406, 408 to the inner longitudinal edge 107*b* of the first belt laminate 406. And the second cut line 416 may extend a distance TW in the cross direction from the inner longitudinal edge 109*b* of the second belt laminate 408 to inner longitudinal edge 107*b* of the first belt laminate 406 without crossing the inner longitudinal edge 107*b*. As such, in some configurations, the width TW of the trim material 412 may be the equal to or substantially equal to the width W3 of the uncovered region 410. In some configurations, the second cut line 416 may extend a distance TW in the cross direction from the inner longitudinal edge 109*b* of the second belt laminate 408 that is less than the width W3 of the uncovered region 410. And in some configurations, the second cut line 416 may extend a distance TW in the cross direction from the inner longitudinal edge 109*b* of the second belt laminate 408 that is greater than the width W3 of the uncovered region 410. As such, the second cut line 416 may cross the inner longitudinal edge 107*b* of the first belt laminate 406, and thus, the trim material 412 may include a portion of the first belt laminate 406 as well as the second belt laminate 408.

Although the cutting apparatus 338 may be configured to cut discrete absorbent articles 100 from the continuous length of absorbent articles 400 while at the same time forming contoured and/or shaped front and/or back elastic belts 106, 108 on the absorbent articles 100, it is to be appreciated that the process and apparatuses herein may be configured to perform these steps at different times. For example, the process may be configured with a separate trim removal unit that forms the contoured and/or shaped front and/or back elastic belts 106, 108 on the absorbent articles 100 before cutting discrete absorbent articles 100 from the continuous length of absorbent articles 400. In some embodiments, the separate trim removal or contouring cut may be performed after the apparatus 334 operates to bond an overlap area 362, thus creating discrete bonds 336*a*, 336*b*. In other embodiments, the separate trim removal or contouring cut may be performed after the folding apparatus 332 folds the chassis also positions the wearer facing surface 312 of the second belt laminate 408 extending between each chassis 102 in a facing relationship with the wearer facing surface 312 of the first belt laminate 406 extending between each chassis 102, and before the apparatus 334 operates to bond an overlap area 362, thus creating discrete bonds 336*a*, 336*b*.

As discussed in more detail below, converting apparatus 300 may control the relative placement of first elastic belt 106, second elastic belt 108, and/or chassis 102 during the assembly process. For example, in some configurations, the relative placement of first elastic belt 106, second elastic belt 108, and/or chassis 102 may be controlled to align the portions Gp1, Gp2, Gp3 of the first and/or second printed stripes G1, G2 in a desired manner. For example, as shown in FIG. 4, the converting apparatus may include a controller 600 adapted to change the machine direction speeds and/or cross direction positions of advancing elastic laminates and/or chassis. Such changes machine direction speeds and/or cross direction positions may be based on the detection of registration features Rf. In turn, the changes in machine direction speeds and/or cross direction positions may alter the relative alignment of the portions Gp1, Gp2, Gp3 of the first and/or second printed stripes G1, G2.

As shown in FIGS. 11 and 14, an inspection system 600 may be configured to interact with, monitor, and/or control the converting line 300. As shown in FIG. 2 and as described in more detail below, various sensors 602 and other devices may be arranged adjacent the converting line 300 may communicate with a controller 604. Based on such communications, the controller 604 may monitor and affect various operations on the converting line 300. For example, the controller may send various types of control commands 1000 to the converter line, such as speed change commands based on communications with the sensors 602. In some embodiments, the control commands 1000 may be in the form of reject commands communicated to the reject system 326. In the systems and methods described herein, the controller 604 may include one or more computer systems. The computer system may, for example, include one or more types of programmable logic controller (PLC) and/or personal computer (PC) running software and adapted to communicate on an EthernetIP network. Some embodiments may utilize industrial programmable controllers such as the Siemens S7 series, Rockwell ControlLogix, SLC or PLC 5 series, or Mitsubishi Q series. The aforementioned embodiments may use a personal computer or server running a control algorithm such as Rockwell SoftLogix or National Instruments Labview or may be any other device capable of receiving inputs from sensors, performing calculations based on such inputs and generating control actions through servomotor controls, electrical actuators or electro-pneumatic, electrohydraulic, and other actuators. Process and product data may be stored directly in the controller or may be located in a separate data historian. In some embodiments, the historian is a simple data table in the controller, in other embodiments, the historian may be a relational or simple database. Common historian applications include Rockwell Automation Factory Talk Historian, General Electric Proficy Historian, OSI PI, or any custom historian that may be configured from Oracle, SQL or any of a number of database applications.

Figure 6:
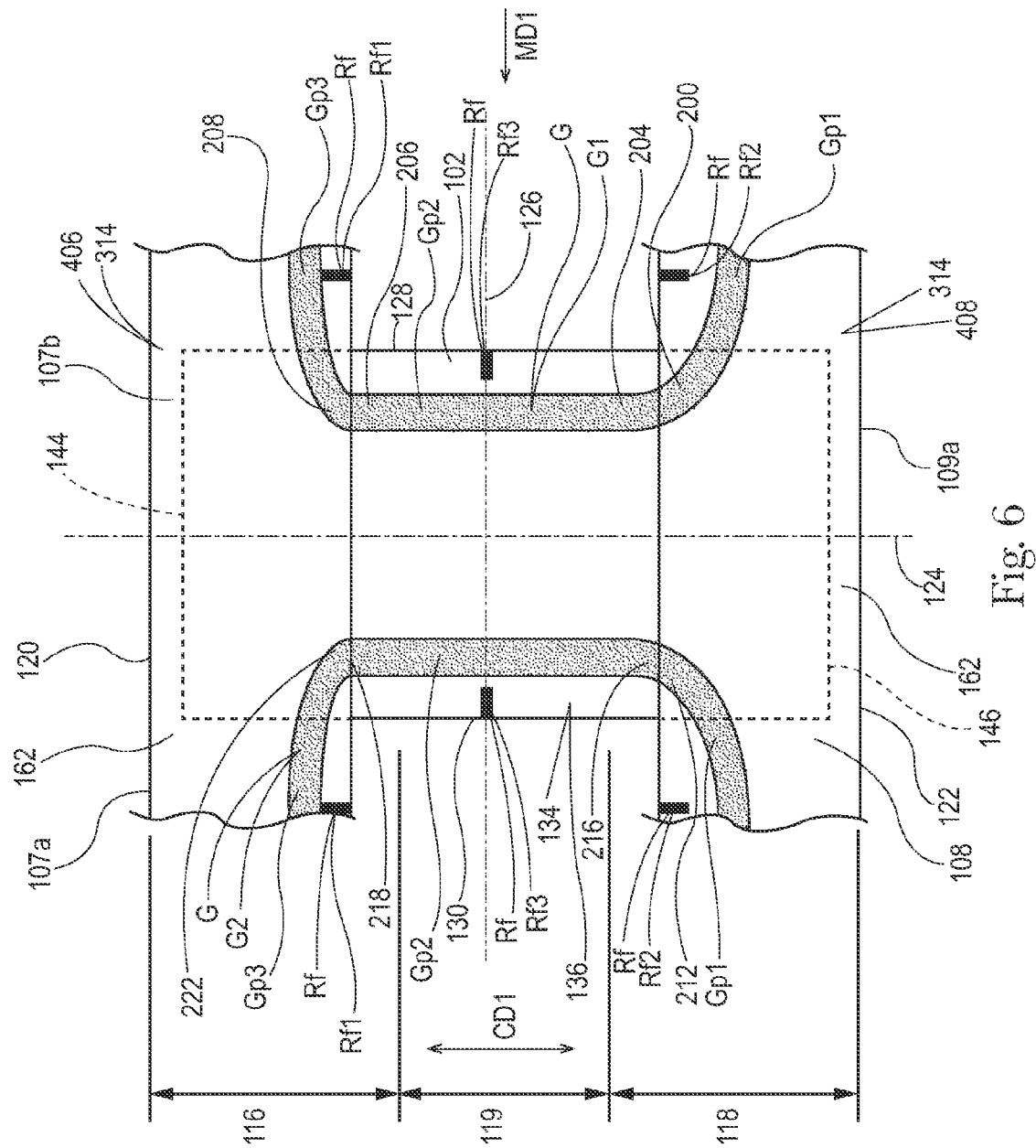
FIG. 6 is a detailed view of a continuous length of absorbent articles showing relative placement of registration features along the first machine direction and first cross direction.

As shown in FIGS. 4-6, the first and/or second elastic belt laminates 406, 408 and/or the continuous length of chassis assemblies 302 may include registration features Rf. For example, the first belt laminate 406 may include registrations features Rf1 arranged along the first machine direction MD1, and the second belt laminate 408 may include registrations features Rf2 arranged along the first machine direction MD1. In addition, the continuous length of chassis assemblies 302 may include registration features Rf3 arranged along the second machine direction MD2.

It is to be appreciated that registration features Rf may be configured in different ways. Registration features Rf may include any signaling mechanism that is recognizable by a machine. For example, registration features Rf may be in the form of printed graphics. In some configurations, the registration features Rf may include a physical discontinuity such as notch, a protrusion, a depression, or a hole formed in a substrate and/or components. In some configurations, the registration features Rf may include a region of magnetic discontinuity, electrical discontinuity, electromagnetic discontinuity, and/or any combination thereof. Some registration features Rf may provide an optical marker that operates on the basis of providing detectable changes in intensities of visible and/or non-visible wavelengths of light. Various examples of registration features are provided in U.S. Pat. Nos. 5,286,543; 6,444,064; and 6,955,733. Registration features Rf may be configured to operatively indicate the boundaries between virtual products, and in some configurations, the registration features Rf are regularly spaced at substantially equal intervals along machine direction of a substrate. As shown in FIGS. 5A and 5C, the registration features Rf may be positioned adjacent lateral side edges of the substrates. It is also to be appreciated that the registration features may be located in various positions on the various diaper components other than what is depicted herein. In addition, it is to be appreciated that instead of having separate graphics and registrations features, all or portions of the graphics may be composed of registration features.

The systems and methods herein may utilize various types of sensors to monitor the substrates and components traveling through the converting line 300. As shown in FIG. 4, various types of inspection sensors 602 may be used to perform various functions. For example, inspection sensors 602 may be used to detect registration features Rf, the relative placement of substrates and/or components, and various types of defects. Based on the detections of the inspection sensors 602, feedback signals from the inspection sensors may be communicated to the controller 600. For example, a sensor 602 can be configured to detect a registration feature Rf on a substrate and communicate an inspection parameter corresponding with the detection of the registration feature to the controller 600. The controller 600 receives the feedback signals from the sensors and compares the feedback signal with setpoints. Based on the comparison, the controller may change the machine direction speeds and/or cross directional positions of the substrates. It is also to be appreciated that various types of controllers and inspection sensors can be configured in various ways and with various algorithms to provide various types of data and perform various functions, for example, such as disclosed in U.S. Pat. Nos. 5,286,543; 5,359,525; 6,801,828; 6,820,022; 7,123,981; 8,145,343; 8,145,344; and 8,244,393; and European Patent No. EP 1528907B1, all of which are incorporated by reference herein.

It is to be appreciated that various different types of inspection sensors 602 may be used to detect registration features Rf and monitor the substrates and components while advancing through the converting line 300. For example, inspection sensors 602 may be configured as photo-optic sensors that receive either reflected or transmitted light and serve to determine the presence or absence of a specific material; metal-proximity sensors that use electromagnetic to determine the presence or absence of a ferromagnetic material; capacitive or other proximity sensors using any of a number of varied technologies to determine the presence or absence materials. Inspection sensors 602 may also be configured as vision systems and other sub-processing devices to perform detection and, in some cases, logic to more accurately determine the status of an inspected product. Particular examples of inspections sensors 602 may include simple vision based sensors such as Cognex Checker series, integrated smart camera systems such as Cognex Insight, DVT Legend or Keyence smart cameras, component vision systems such as National Instruments CVS vision systems or PC based vision system such as Cognex VisionPro or any other vision system software which can run on a PC platform.

As shown in FIG. 4, the inspection sensors 602 are connected with the controller 600 through a communication network 604, which allows the inspection sensors 602 to communicate inspection parameters to the controller 600. It should also be appreciated that the inspection parameters may be provided from inspection sensors 602 in various forms. In one embodiment, inspection parameters may be in the form "results," such as for example, provided from a sensor state change resulting in a binary input corresponding with the detected presence or absence of a registration feature. In some embodiments, inspection parameters may be provided in the form of measurements and/or numerical indications of detected positions of registration features relative to components and/or substrates; and/or numerical indications of the positions of components and/or substrates relative to other physical or virtual references. In other embodiments, inspection parameters may be in the form of images transferred via a standard protocol such as ftp (File Transfer Protocol), DDE (Dynamic Data Exchange), or OPC (Object Linking and Embedding for Process Control).

As mentioned above, the controller 600 may be adapted to control the relative placement of first elastic belt 106, second elastic belt 108, and/or chassis 102 during the assembly process based on detections of the registration features Rf on the first and/or second belt laminates 406, 408 and/or continuous length of chassis assemblies 302. For the purposes of the following discussion, with reference to FIGS. 4 and 6, the second belt laminate 408 may advance in the first machine direction MD1 at a speed S1; and the continuous length of chassis assemblies 302 may advance in the second machine direction MD2 at a speed S2; and first belt laminate 406 may advance in the first machine direction MD1 at a speed S3.

In an example, with continued reference to FIGS. 4 and 6, the controller 600 may be configured to change the placement of the registration features Rf2 and Rf3 relative to each other along the first machine direction MD1 by adjusting the speed S1 of the second belt laminate 408 and/or shifting the continuous length of chassis assemblies 302 in the second cross direction CD2. In addition, the controller 600 may be configured to change the placement of the registration features Rf2 and Rf3 relative to each other along the first cross direction CD1 by adjusting the speed S2 of the continuous length of chassis assemblies 302 and/or shifting the second belt laminate 408 in the first cross direction CD1. In yet another example, the controller 600 may be configured to change the placement of the registration features Rf2 and Rf3 relative to each other along the first cross direction CD1 by adjusting an angular velocity of the carrier apparatus 308, which in turn, adjusts the speed of the discrete chassis 102. As also discussed above with reference to FIGS. 4, 5B1, 5B2, and 6, the carrier apparatus 308 may be configured to change the chassis orientation. Thus, in yet another example, the carrier apparatus 308 may turn each chassis 102 such that the lateral axis 126 of the chassis 102 is parallel or generally parallel with the first machine direction MD1. As such, the controller 600 may also be configured to change the placement of the registration features Rf2 and Rf3 (or Rf1) relative to each other along the first cross direction CD1 and/or machine direction MD1 by adjusting how much the carrier apparatus 308 may turn each chassis 102. It is also to be appreciated that the carrier apparatus 308 may be configured with transfer members that turn in opposite directions, and thus operates to turn each consecutive chassis in opposite directions, such as disclosed for example, in U.S. patent application Ser. No. 14/038,821, entitled "Method and Apparatus for Changing the Orientation of an Absorbent Article," filed on Sep. 27, 2013, which is hereby incorporated by reference. In turn, changing the relative placement of the registration features changes the relative placement of the portions of the graphics. For example, changing the relative placement of the registration features Rf2 and Rf3 changes the relative placement of the first portion Gp1 and the second portion Gp2 of the first stripe G1 and the second stripe G2. Thus, the relative placement of registration features Rf2 and Rf3 may be controlled to align the portions Gp2 and Gp3 of the first and/or second printed stripes G1, G2 in a desired manner.

In an additional example, the controller 600 may be configured to change the placement of the registration features Rf1 and Rf3 relative to each other along the first machine direction MD1 by adjusting the speed S3 of the first belt laminate 406 and/or shifting the continuous length of chassis assemblies 302 in the second cross direction CD2. In addition, the controller 600 may be configured to change the placement of the registration features Rf1 and Rf3 relative to each other along the first cross direction CD1 by adjusting the speed S2 of the continuous length of chassis assemblies 302 and/or shifting the first belt laminate 406 in the first cross direction CD1. In yet another example, the controller 600 may be configured to change the placement of the registration features Rf1 and Rf3 relative to each other along the first cross direction CD1 by adjusting an angular velocity of the carrier apparatus 308, which in turn, adjust the speed of the discrete chassis 102. In turn, changing the relative placement of the registration features Rf1 and Rf3 changes the relative placement of the third portion Gp3 and the second portion Gp2 of the first stripe G1 and the second stripe G2. Thus, the relative placement of registration features Rf1 and Rf3 may be controlled to align the portions Gp2 and Gp3 of the first and/or second printed stripes G1, G2 in a desired manner.

It is to be appreciated that in some configurations, the second belt laminate 408; the first belt laminate 406; and the continuous length of chassis assemblies 302 may all include registration features Rf. In some configurations, the continuous length of chassis assemblies 302 may include registration features Rf, whereas only one of the second belt laminate 408 and the first belt laminate 406 may include registration features Rf. It is also to be appreciated that the registrations features Rf may be removed from the second belt laminate 408; the second elastic belt 108; the first belt laminate 406; the first elastic belt 106; the continuous length of chassis assemblies 302; and/or the discrete chassis 102 at various stages of the assembly process. For example, as shown in FIGS. 5E1 and 5F1, the registrations features Rf2 are removed along with the trim material 412.

Figure 7:
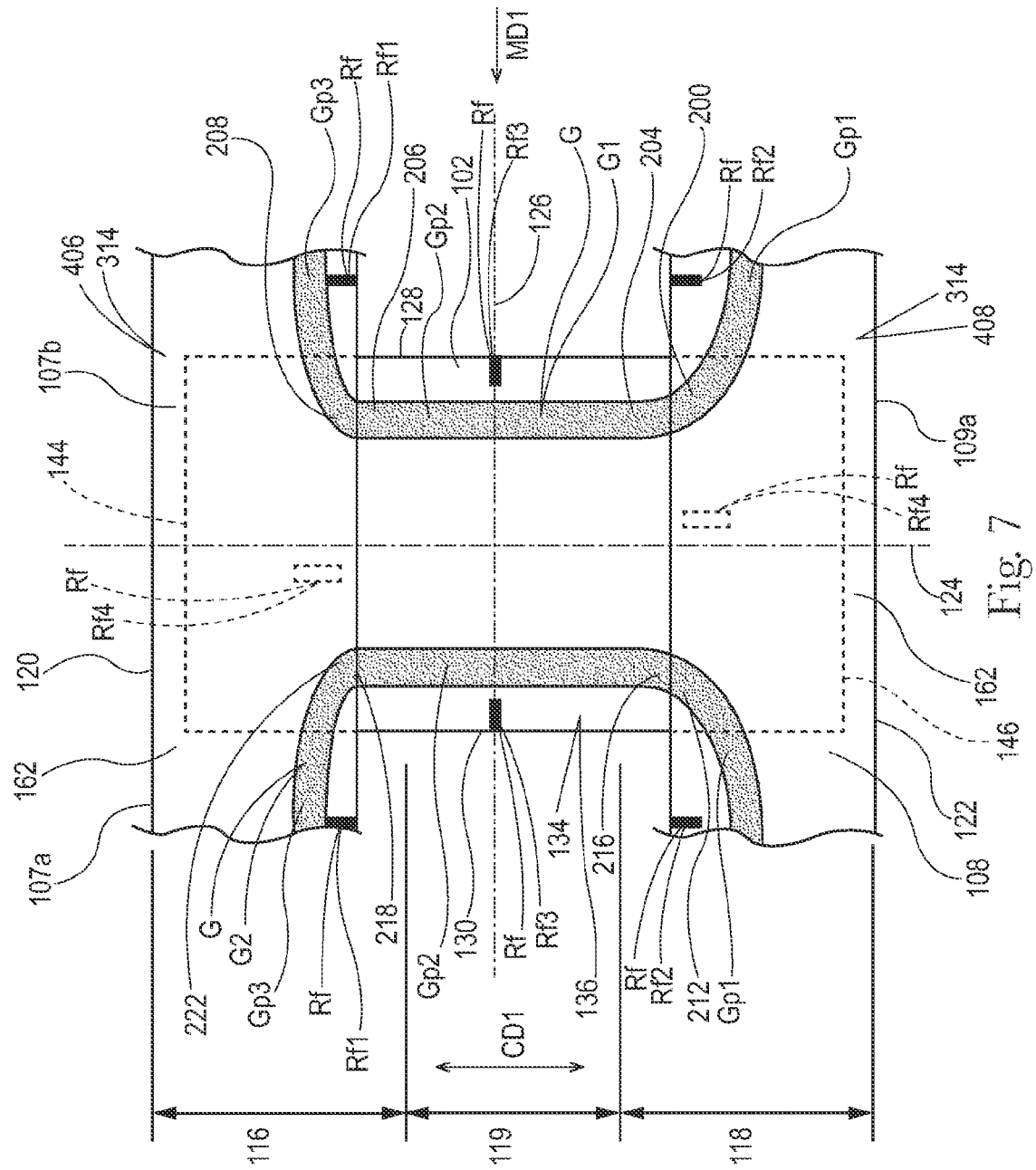
FIG. 7 is a detailed view of a continuous length of absorbent articles showing relative placement of registration features along the first machine direction and first cross direction.

It is to be appreciated that the various components discussed above may include one or more registration features. For example, although the chassis 102 in FIG. 6 is depicted as having two laterally opposing registration features Rf3 located generally in the crotch region 119, the chassis 102 may be configured with a single registration feature Rf that may be located in various regions, such as either the waist regions 116, 118 or the crotch region 119. In another example such as shown in FIG. 7, the chassis may include one or more registration features Rf3 in the crotch region and one more registration features Rf4 in one or both waist regions 116, 118. In such a configuration, the registration features Rf3 may be used to adjust placement of the chassis 102 along the first cross direction CD1, and the registration feature Rf4 may be used to adjust placement of the chassis 102 along the first machine direction MD1. For example, the relative placement of registration features Rf1 and Rf4 in the first waist region 116 may be controlled to align the portions Gp2 and Gp3 of the first and/or second printed stripes G1, G2 along the first machine direction MD1. And the relative placement of registration features Rf2 and Rf4 in the second waist region 118 may be controlled to align the portions Gp1 and Gp2 of the first and/or second printed stripes G1, G2 in along the first machine direction MD1.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for assembling disposable pant diapers, each pant diaper comprising a chassis having a first end region and an opposing second end region separated from each other by a central region, and having a longitudinal axis and a lateral axis, the chassis comprising: a topsheet, a backsheet, and an absorbent core disposed between the topsheet and the backsheet, the method comprising the steps of:

advancing a first continuous substrate in a first machine direction at a first speed, the first continuous substrate defining a width in a first cross direction, wherein the first continuous substrate includes first registration features arranged along the first machine direction;

advancing a second continuous substrate in a second machine direction at a second speed, the second continuous substrate defining a width in a second cross direction, wherein the second continuous substrate includes second registration features arranged along the second machine direction;

cutting the second continuous substrate into discrete chassis, wherein each chassis advances such that the longitudinal axis is parallel with the second machine direction;

turning each chassis such that the lateral axis is parallel with the first machine direction;

bonding the first end regions of each chassis with the first continuous substrate;

detecting positions of first and second registration features relative to each other along the first machine direction and along the first cross direction;

changing placement of first and second registration features relative to each other along the first machine direction for each chassis subsequently bonded to the first continuous substrate based on detections of first and second registration features relative to each other on chassis previously bonded to the first continuous substrate by at least one of: adjusting the first speed of the first continuous substrate and shifting the second continuous substrate in the second cross direction; and changing the placement of first and second registration features relative to each other along the first cross direction for each chassis subsequently bonded to the first continuous substrate based on detections of first and second registration features relative to each other on chassis previously bonded to the first continuous substrate by at least one of: shifting the first continuous substrate in the first cross direction and adjusting the second speed of the second continuous substrate in the second machine direction.

2. The method of claim 1, wherein the second speed is greater than the first speed.

3. The method of claim 2, wherein the step of turning each chassis further comprises slowing each chassis from the second speed to the first speed.

4. The method of claim 1, further comprising the steps of:
advancing a third continuous substrate in the first machine direction at a third speed, the third continuous substrate defining a width in the first cross direction; and
bonding the second end regions of each chassis with the third continuous substrate.

5. The method of claim 4, wherein the third continuous substrate includes third registration features arranged along the first machine direction, and further comprising the step of changing the placement of the third and second registration features relative to each other along the first machine direction by at least one of: adjusting the third speed of the third continuous substrate and shifting the second continuous substrate in the second cross direction.

6. The method of claim 5, further comprising the step of changing the placement of the third and second registration features relative to each other along the first cross direction by at least one of: shifting the third continuous substrate in the first cross direction and adjusting the second speed of the second continuous substrate in the second machine direction.

7. The method of claim 4, further comprising the steps of:
folding each chassis along the lateral axis to position the first continuous substrate into a facing relationship with the third continuous substrate;
bonding the first continuous substrate with the third continuous substrate at discrete bond regions; and
cutting the first and third continuous substrates along the first cross direction to form discrete pant diapers.

8. The method of claim 1, further comprising the step of: cutting discrete pieces of trim material from the first continuous substrate.

9. The method of claim 8, wherein the step of cutting discrete pieces of trim material further comprises removing at least portions of the first registration features from the first continuous substrate.

10. A method for assembling disposable pant diapers, each pant diaper comprising a chassis having a first end region and an opposing second end region separated from each other by a central region, and having a longitudinal axis and a lateral axis, the chassis comprising: a topsheet, a backsheet, and an absorbent core disposed between the topsheet and the backsheet, the method comprising the steps of:

advancing a first continuous elastic laminate in a first machine direction at a first speed, the first continuous elastic laminate defining a width in a first cross direction, wherein the first continuous elastic laminate includes first registration features arranged along the first machine direction;

advancing a second continuous elastic laminate in a second machine direction at a second speed, the second continuous elastic laminate defining a width in a second cross direction, wherein the second continuous elastic laminate includes second registration features arranged along the second machine direction;

cutting the second continuous elastic laminate into discrete chassis, wherein each chassis advances such that the longitudinal axis is parallel with the second machine direction;

turning each chassis such that the lateral axis is parallel with the first machine direction;

bonding the first end regions of each chassis with the first continuous elastic laminate;

advancing a third continuous elastic laminate in the first machine direction, the third continuous elastic laminate defining a width in the first cross direction, wherein the third continuous elastic laminate includes third registration features arranged along the first machine direction; and bonding the second end regions of each chassis with the third continuous elastic laminate;

changing positions of the first, second, and third registration features relative to each other along the first machine direction; and changing the positions of the first, second, and third registration features relative to each other along the first cross direction.

11. The method of claim 10, further comprising the step of: changing positions of the first and second registration features relative to each other along the first machine direction by at least one of: adjusting the first speed of the first continuous elastic laminate and shifting the second continuous elastic laminate in the second cross direction.

12. The method of claim 10, further comprising the step of: changing the positions of the first and second registration features relative to each other along the first cross direction by at least one of: shifting the first continuous elastic laminate in the first cross direction and adjusting the second speed of the second continuous elastic laminate in the second machine direction.

13. The method of claim 10, further comprising the steps of:
folding each chassis along the lateral axis to position the first continuous elastic laminate into a facing relationship with the third continuous elastic laminate;
bonding the first continuous elastic laminate with the third continuous elastic laminate at discrete bond regions; and
cutting the first and third continuous elastic laminates along the first cross direction to form discrete pant diapers.

14. The method of claim 10, further comprising the step of removing at least portions of the first registration features from the first continuous elastic laminate.

15. A method for assembling disposable pant diapers, each pant diaper comprising a chassis having a first end region and an opposing second end region separated from each other by a central region, and having a longitudinal axis and a lateral axis, the chassis comprising: a topsheet, a backsheet, and an absorbent core disposed between the topsheet and the backsheet, the method comprising the steps of:
advancing a first continuous substrate in a first machine direction at a first speed, the first continuous substrate having an outer longitudinal edge and an inner longitudinal edge defining a width in a first cross direction, wherein the first continuous substrate includes first registration features arranged along the first machine direction;
advancing a second continuous substrate in a second machine direction at a second speed, the second continuous substrate defining a width in a second cross direction, wherein the second continuous substrate includes second registration features arranged along the second machine direction;
cutting the second continuous substrate into discrete chassis, wherein each chassis advances such that the longitudinal axis is parallel with the second machine direction;
turning each chassis such that the lateral axis is parallel with the first machine direction;
bonding the first end regions of each chassis with the first continuous substrate;
advancing a third continuous substrate in the first machine direction, the third continuous substrate having an outer longitudinal edge and an inner longitudinal edge defining a width in the first cross direction; and
bonding the second end regions of each chassis with the third continuous substrate;
folding each chassis along the lateral axis to position the first continuous substrate into a facing relationship with the third continuous substrate and defining uncovered regions of the first continuous substrate intermittently spaced between the chassis along the first machine direction and having a width extending in the first cross direction defined by a distance extending between the inner longitudinal edge of the first continuous elastic laminate and the inner longitudinal edge of the third continuous elastic laminate; and
removing at least portions of the first registration features by cutting discrete pieces of trim material from the uncovered regions of the first continuous substrate.

16. The method of claim 15, wherein the step of removing the first registration features further comprises cutting the first and third continuous substrates in the first cross direction to form discrete pant diapers.

17. The method of claim 16, wherein the width of the first continuous substrate is a substantially constant width, W1, in the first cross direction; wherein the width of the third continuous substrate is a substantially constant width, W2, in the first cross direction; and wherein W1 is greater than W2.

18. The method of claim 17, further comprising the step of changing positions of the first and second registration features relative to each other along the first machine direction by at least one of: adjusting the first speed of the first continuous substrate and shifting the second continuous substrate in the second cross direction.

19. The method of claim 18, further comprising the step of changing the positions of the first and second registration features relative to each other along the first cross direction by at least one of: shifting the first continuous substrate in the first cross direction and adjusting the second speed of the second continuous substrate in the second machine direction.

20. The method of claim 19, wherein the first registration features extend in the first cross direction between inner longitudinal edge of the first continuous substrate and the inner longitudinal edge of the third continuous substrate.

21. A method for assembling disposable pant diapers, each pant diaper comprising a chassis having a first end region and an opposing second end region separated from each other by a central region, and having a longitudinal axis and a lateral axis, the chassis comprising: a topsheet, a backsheet, and an absorbent core disposed between the topsheet and the backsheet, the method comprising the steps of:
advancing a first continuous substrate in a first machine direction at a first speed, the first continuous substrate defining a width in a first cross direction, wherein the first continuous substrate includes first registration features arranged along the first machine direction;
advancing a second continuous substrate in a second machine direction at a second speed, the second continuous substrate defining a width in a second cross direction, wherein the second continuous substrate includes second registration features arranged along the second machine direction;
cutting the second continuous substrate into discrete chassis, wherein each chassis advances such that the longitudinal axis is parallel with the second machine direction;
turning each chassis such that the lateral axis is parallel with the first machine direction;
detecting positions of first and second registration features relative to each other along the first machine direction and along the first cross direction;
changing placement of first and second registration features relative to each other along the first machine direction for each chassis based on detections of first and second registration features relative to each other by at least one of: adjusting the first speed of the first continuous substrate and shifting the second continuous substrate in the second cross direction;
changing placement of first and second registration features relative to each other along the first cross direction for each chassis based on detections of first and second registration features relative to each other by at least one of: shifting the first continuous substrate in the first cross direction and adjusting the second speed of the second continuous substrate in the second machine direction; and subsequently bonding the first end regions of each chassis with the first continuous substrate.

22. The method of claim 21, wherein the second speed is greater than the first speed.

23. The method of claim 22, wherein the step of turning each chassis further comprises slowing each chassis from the second speed to the first speed.

24. The method of claim 21, further comprising the steps of:

advancing a third continuous substrate in the first machine direction at a third speed, the third continuous substrate defining a width in the first cross direction; and bonding the second end regions of each chassis with the third continuous substrate.

25. The method of claim 24, wherein the third continuous substrate includes third registration features arranged along the first machine direction, and further comprising the step of changing the placement of the third and second registration features relative to each other along the first machine direction by at least one of: adjusting the third speed of the third continuous substrate and shifting the second continuous substrate in the second cross direction.

26. The method of claim 25, further comprising the step of changing the placement of the third and second registration features relative to each other along the first cross direction by at least one of: shifting the third continuous substrate in the first cross direction and adjusting the second speed of the second continuous substrate in the second machine direction.

27. The method of claim 24, further comprising the steps of:

folding each chassis along the lateral axis to position the first continuous substrate into a facing relationship with the third continuous substrate;

bonding the first continuous substrate with the third continuous substrate at discrete bond regions; and cutting the first and third continuous substrates along the first cross direction to form discrete pant diapers.

28. The method of claim 21, further comprising the step of: cutting discrete pieces of trim material from the first continuous substrate.

29. The method of claim 28, wherein the step of cutting discrete pieces of trim material further comprises removing at least portions of the first registration features from the first continuous substrate.

* * * * *